(12) United States Patent
Heyl et al.

(10) Patent No.: US 10,940,484 B2
(45) Date of Patent: Mar. 9, 2021

(54) CONDUCTIVE INKS AND METHOD OF MANUFACTURE

(71) Applicant: BioLink Systems, LLC, Covington, KY (US)

(72) Inventors: Ken Heyl, Birminghan, AL (US); Drew Bredar, Louisville, KY (US); Roger King, Hamilton, OH (US)

(73) Assignee: BioLink Systems LLC, Covington, KY (US)

( * ) Notice: Subject to any disclaimer, the term of this patent is extended or adjusted under 35 U.S.C. 154(b) by 11 days.

(21) Appl. No.: 16/522,047

(22) Filed: Jul. 25, 2019

(65) Prior Publication Data

US 2021/0022927 A1 Jan. 28, 2021

(51) Int. Cl.

| | | |
|---|---|---|
| *B02C 23/38* | (2006.01) |
| *B02C 17/00* | (2006.01) |
| *B02C 23/18* | (2006.01) |
| *A61F 13/42* | (2006.01) |
| *B02C 17/16* | (2006.01) |
| *B02C 17/18* | (2006.01) |
| *C09C 1/46* | (2006.01) |
| *C09D 11/52* | (2014.01) |
| *C09C 1/48* | (2006.01) |
| *C09C 3/04* | (2006.01) |

(52) U.S. Cl.
CPC .............. *B02C 23/38* (2013.01); *B02C 17/00* (2013.01); *B02C 17/163* (2013.01); *B02C 17/1815* (2013.01); *B02C 23/18* (2013.01); *C09C 1/46* (2013.01); *C09C 1/48* (2013.01); *C09C 3/041* (2013.01); *C09D 11/52* (2013.01); *A61F 13/42* (2013.01); *A61F 2013/424* (2013.01); *A61F 2013/426* (2013.01); *A61F 2013/429* (2013.01)

(58) Field of Classification Search
CPC ....... B02C 23/38; B02C 17/00; B02C 17/163; B02C 17/1815; C09D 7/40; C09D 7/60; C09D 7/61; C09D 11/52; H01L 31/04; H01L 31/24
USPC ............................................ 241/29; 252/500
See application file for complete search history.

(56) References Cited

U.S. PATENT DOCUMENTS

| | | |
|---|---|---|
| 7,053,781 B1 | 5/2006 | Haire et al. |
| 7,977,529 B2 | 7/2011 | Bergman et al. |
| 7,996,148 B2 | 8/2011 | Bergman et al. |
| 8,145,422 B2 | 3/2012 | Bergman et al. |
| 8,788,195 B2 | 7/2014 | Bergman et al. |
| 9,107,776 B2 | 8/2015 | Bergman et al. |
| 9,224,102 B2 | 12/2015 | Bergman et al. |
| 9,283,123 B2 | 3/2016 | Bergman et al. |
| 9,314,381 B2 | 4/2016 | Bergman et al. |

(Continued)

*Primary Examiner* — Faye Francis
*Assistant Examiner* — Smith Oberto Bapthelus
(74) *Attorney, Agent, or Firm* — Chris Tanner; FYPA PLLC

(57) ABSTRACT

An ink mixture is manufactured by mixing carbon, graphite, and solvents in a mixing system which may include a Cowles disperser. The conductive portions (e.g. carbon, graphite) are evenly and universally dispersed, because an even dispersal means the conductivity of the resulting conductive strip (electrode) will be even, consistent, and reliable. The various embodiments of the ink mixture comprise a blend of different conductive pigments, including but not limited to carbon black and graphite. These embodiments must be grinded until below 6.5 Microns in particle size.

16 Claims, 22 Drawing Sheets

(56) References Cited

U.S. PATENT DOCUMENTS

| | | | |
|---|---|---|---|
| 9,574,094 B2 * | 2/2017 | Decker | C08L 33/068 |
| 9,646,073 B2 | 5/2017 | Bergman et al. | |
| 9,665,639 B2 | 5/2017 | Bergman et al. | |
| 9,713,554 B2 | 7/2017 | Bergman et al. | |
| 9,913,608 B2 | 3/2018 | Bergman et al. | |
| 10,561,541 B1 * | 2/2020 | Heyl | A61F 13/42 |
| 2011/0135925 A1 * | 6/2011 | Zhamu | D01F 9/12 |
| | | | 428/367 |
| 2014/0339479 A1 * | 11/2014 | Koike | B02C 23/06 |
| | | | 252/514 |
| 2016/0095758 A1 | 4/2016 | Haire et al. | |
| 2018/0022023 A1 * | 1/2018 | Therriault | C09D 7/61 |
| | | | 264/460 |

* cited by examiner

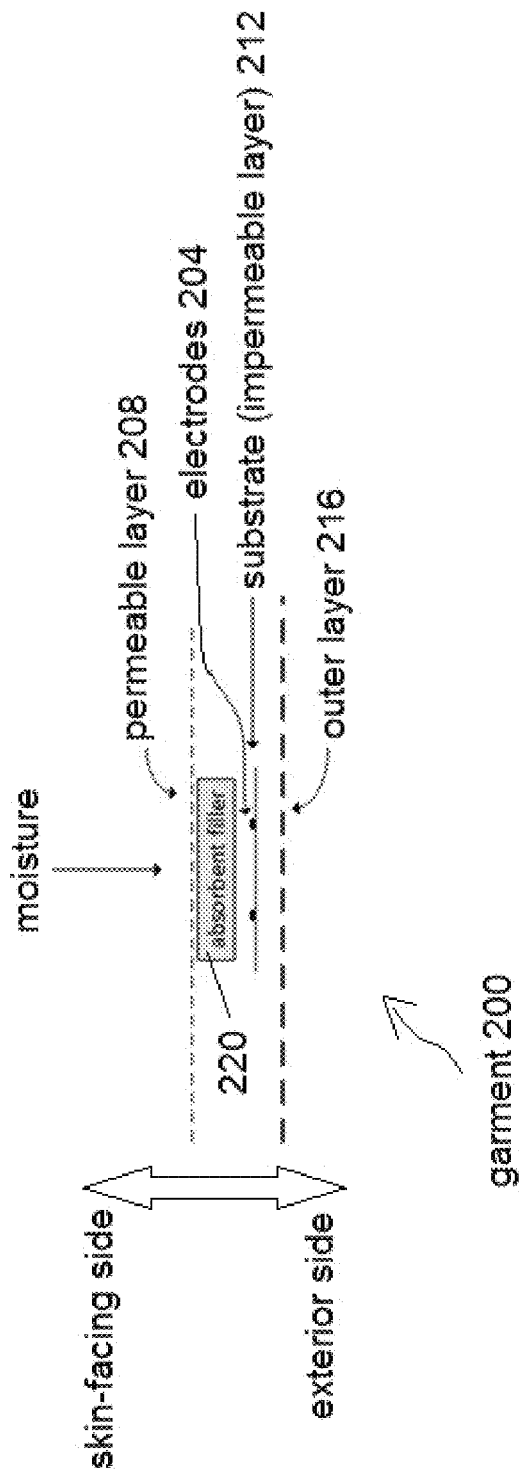
FIG. 2A (cross-sectional view)

locating a wetness sensor having a conductive strip within an underwear brief configuring an electronic module having a micronctonroller and transmitter to be mechanically connectable with the brief and electrically conectable with the wetness sensor mechanically connecting the module to the conductive strip electrically connecting the module to the conductive strip electrically testing the connection between the module and the conductive strip

FIG. 8B

CONDUCTIVE INKS AND METHOD OF MANUFACTURE

BACKGROUND OF THE INVENTION

A shortcoming of existing embodiments of conductive garments is that incorporating conductive threads or fibers into clothing or other textile or paper products may not be compatible with manufacturing in high volume. Consequently, a system and method for inclusion of conductive inks and other materials into clothing or other textile or paper products for the purpose of sensing moisture is discussed, especially where that system is compatible with high volume manufacturing systems.

SUMMARY OF THE INVENTION

A method of adding sensing of moisture and other characteristics into a garment such as a diaper, incontinence garment, brief, or underwear is disclosed. The primary design intent is optimal moisture detection and low per unit cost, including designs for mass manufacturing considerations. The embodiments place various forms of electrodes within a garment, and then, while the garment is worn, measuring the electrical properties of the electrodes to determine if the garment has contacted moisture. A sensor module is located within the garment, and the electrical properties of the sensor element are measured to determine if the garment has contacted moisture. Moisture can include but is not limited to bodily fluids but can also include fluids from the environment. The embodiments herein could be used for sensing incontinence, sensing perspiration, and detecting failure of protective garments.

The target moisture is urine and feces; however, other sources of moisture can also be sensed. Additional analysis capabilities can be added by selecting particular electrodes or additional materials that may react with chemical components of the moisture.

The embodiments herein include detection of moisture in an item worn by or placed near a person and systems and methods for manufacturing the same. Most often this will be a disposable diaper, incontinence garment, brief, or underwear, although embodiments of the combination\system disclosed herein could potentially be used in pads and bandages, and detect types of moisture other than incontinence.

BRIEF DESCRIPTION OF THE DRAWINGS

FIG. 2A shows a cross-sectional view of an embodiment of a garment;

FIG. 8B is a flowchart showing a method of testing the embodiments.

DETAILED DESCRIPTION OF THE PREFERRED EMBODIMENTS

The following definitions will apply throughout this disclosure.

Garment: a diaper, incontinence device, brief, underwear, or other article of clothing, bandage, or pad containing electrodes. Within this disclosure, the expression "diapers", "briefs", or "disposable underwear" will be used interchangeably with the phrase "incontinence garment".

Module: an electronic device attached to the garment and containing a power source, various sensors, and communication circuit.

Electrode: a conductive path connecting the module to a location within the garment being sensed. Within the embodiments herein, two or more electrodes may be used. The electrodes may be the same or different material. Electrodes may provide both connection and sensing functions.

Moisture: a deposition of a single or combination of bodily or other fluids. External sources of moisture may also be sensed.

Substrate: the layer that contains the electrodes.

Contacts: a type of electrical connection to the electrodes, e.g. potentially a place to locate wires or sensors.

Binder or Enhancements: materials that may be added to the garment to improve wetting, adhesion, durability, resistance to oxidation, flexibility and resistance to cracking, or to aid in manufacturing.

Figure 1:
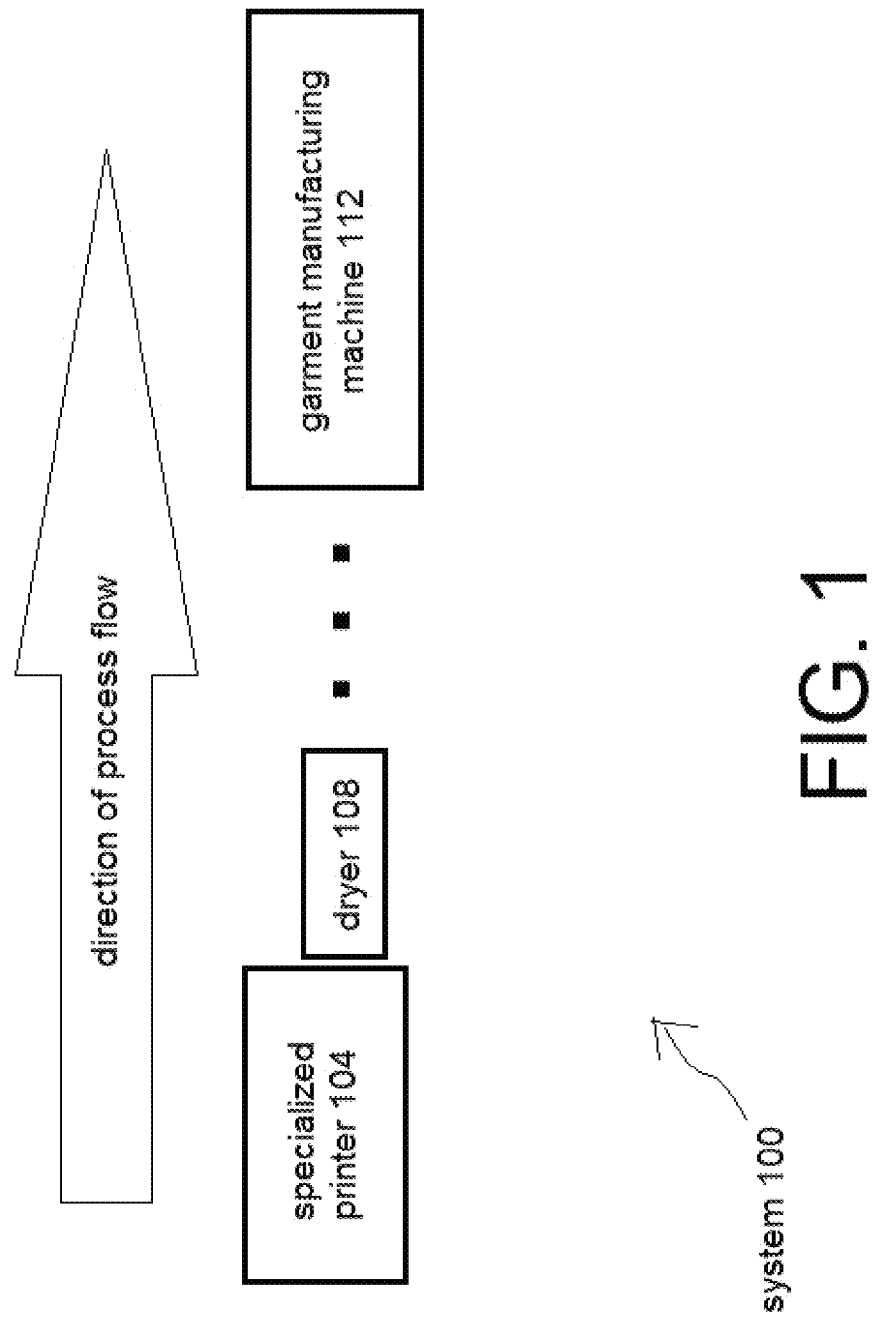
FIG. 1 shows an arrangement of a garment-manufacturing system according to an embodiment.

FIG. 1 shows a (simplified) arrangement of a system 100, in which one or more specialized printers 104, each with a dryer 108 at the back end, work in conjunction with a garment manufacturing machine 112 to create various embodiments of the garment 200 discussed herein. In an embodiment, the specialized printer 104 is a flexographic printer, although other types of printers may also be used. The garment manufacturing machine 112 is intentionally shown to be separated from the printer 104 and dryer 108 by ellipses ( . . . ), and thus may be in an entirely different geographic location, or may be on the same premises. Further, the various manufacturing processes involving the garment manufacturing machine 112, the conductive inks 500 forming the electrodes 204, and the printer\dryer 104\108 may occur at totally different intervals of time and locations.

Machines that make garments such as but not limited to briefs, are often very large (e.g. about a city block long) and can produce garments at great speed, e.g. 1-500 units/minute. In an embodiment, the various features described herein are incorporated into a pre-existing garment manufacturing process, except that a pre-printed poly film (substrate) 212 (FIGS. 2A-2C) is further included. One advantage of such an arrangement is that using the pre-printed poly film substrate 212 described herein will not slow down the manufacturing process whatsoever.

Next, flexographic printing mechanisms are advantageous for low-cost print procedures. Flexographic printing mechanisms are suitable because of their speed, and flexographic printing presses usually have ample drying capacity tacked on to their back end. As such, flexographic printers can print and dry very quickly, so that the finished pre-printed poly film or substrate 212 can be rolled up and won't block (stick together or transfer print) since the substrate 212 is already dry. This is an important feature for the garment 200 in which management and detection of moisture is a consideration.

Flexographic printers are also often implemented in arrangements of multiple print-stations (e.g. printer $104_{1-n}$ and dryer $108_{1-n}$). However, the embodiments herein are not exclusively to multi-printer arrangements, nor are they limited solely to flexographic printing.

In an embodiment, the flexographic printer 104 prints an electrode 204 onto the poly film (substrate) 212, which is then referred to as a pre-printed poly film (substrate) 212. Afterwards, the dryer 108 performs drying on the combination. Upon being sufficiently dry, the pre-printed poly film (substrate) 212 may then be stored, either individually or in groups.

Figure 8A:
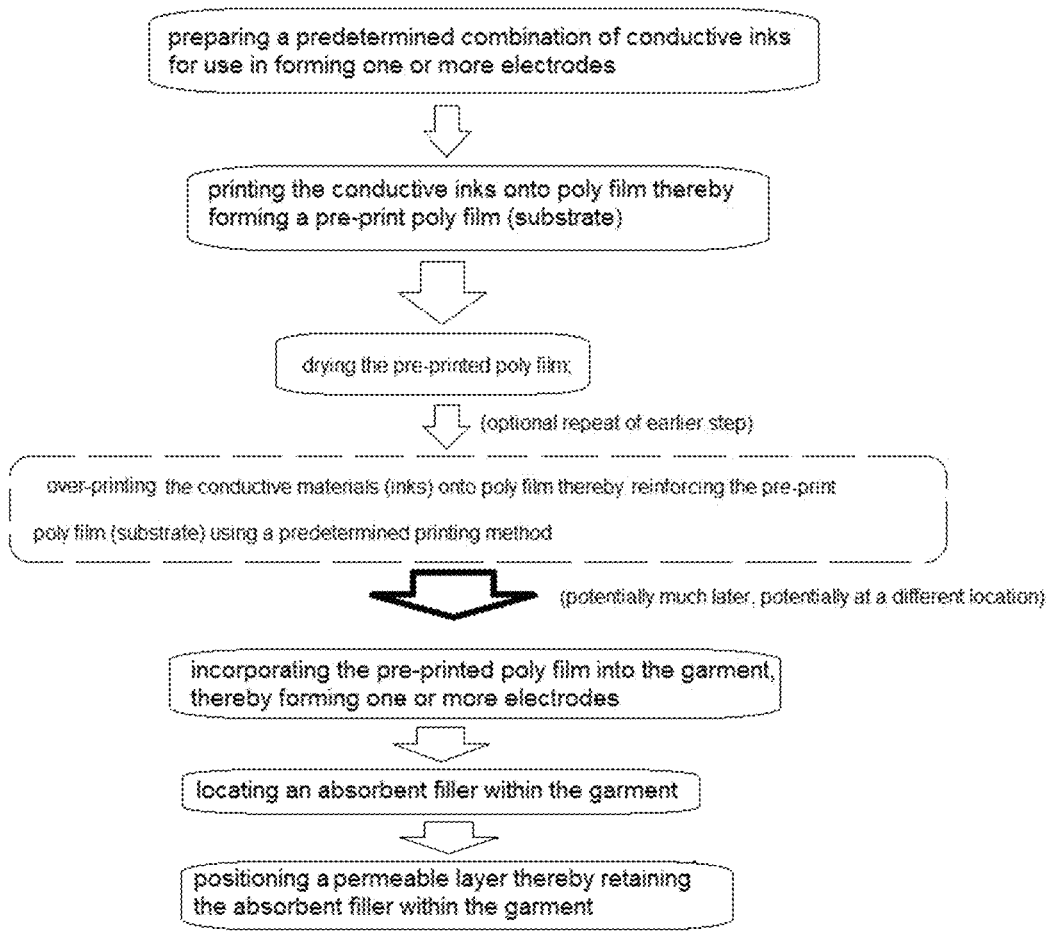
FIG. 8A is a flowchart showing a method of manufacturing the embodiments.

Further, in an embodiment, the pre-printed poly film (substrate) 212 may be (optionally) re-run through a single specialized (e.g. flexographic) printer 104 and dryer 108. Such a re-run or re-printing (over-printing) or double-printing would be at least for the purpose of assuring suitable levels of conductivity, specifically conductivity of the resulting electrode 204. A flowchart of such over-printing is shown within FIG. 8A. Further, as stated, FIG. 8B is a flowchart showing a method of testing the embodiments.

Once the pre-printed poly film (substrate) 212 has completed its processes, including over-printing if suitable, then, either at that time, or (more likely) at a later time, and potentially in a different facility, the pre-printed poly film (substrate) 212 is fed into the garment manufacturing machine 112 as a pre-printed assembly. As part of that feeding process, the pre-printed poly film 212 can be, for example, located at a bottom of a garment 200, underneath the absorbent mass 220 as shown in FIG. 2A. A breathable outer layer 216 is the portion of the garment 200 which is positioned furthest from the human body.

Figure 2B:
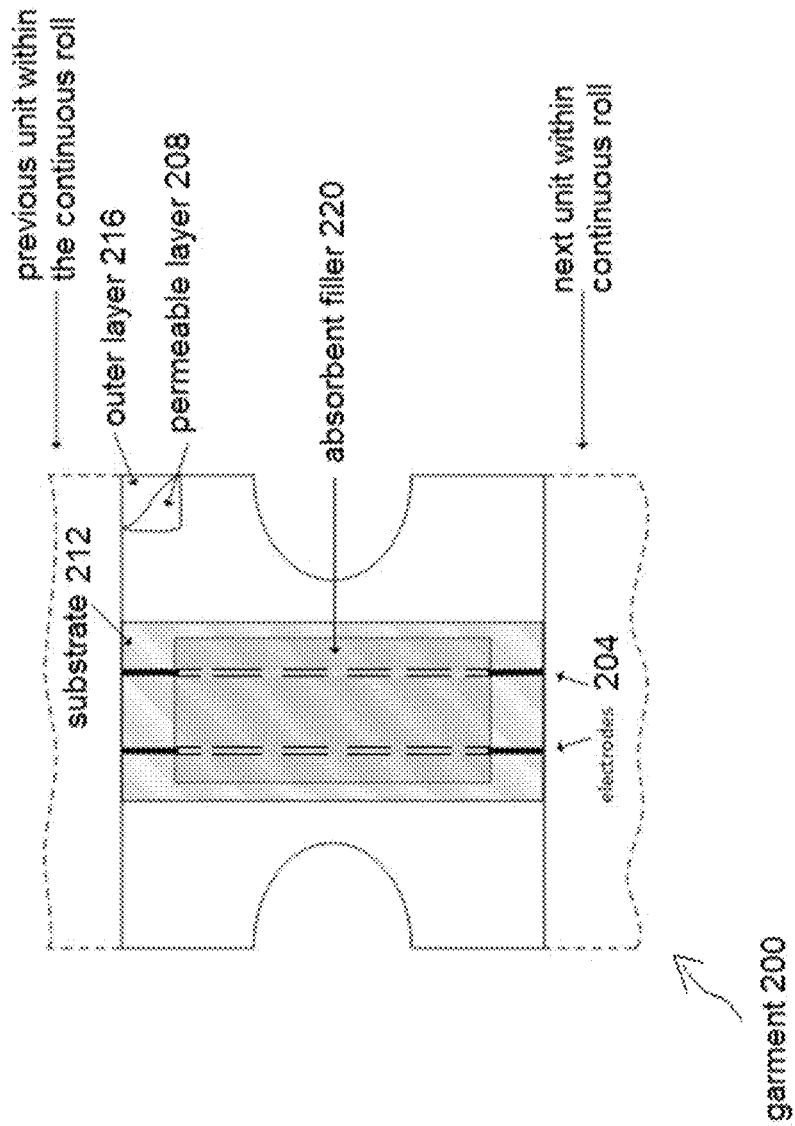
FIG. 2B shows a parallel pattern integrated within a garment in a continuous roll method.

An non-limiting example of a garment 200 is shown at least within FIGS. 2A and 2B.

This arrangement is optimal to prevent the moisture, e.g. urine/feces from soaking thru to a bed, chair, or other surface. The pre-printed poly film (substrate) 212 does not get in the way of or cause any problems for the garment manufacturing machine 112 as the film (substrate) 212 is no thicker & no stiffer than the plain "poly" used in conventional garments. The embodiments shown in FIGS. 2A and 2B are for example only, and the embodiments herein should not be considered as limited thereto.

FIG. 2B illustrates what is meant by "continuous roll", where a roll of garments are shown separated by dashed lines. As the garments 200 are manufactured, the raw materials are combined in a continuous fashion. Most of the layers of the garments 200 are initially on rolls, and are introduced into the process at the appropriate time. The absorbent mass (filler) 220 is introduced into the manufacturing process in the form of "fluff" (raw fibers) which are later formed into various shapes which fit the human anatomy. This mass is laid down on the pre-printed poly film (substrate) 212, and then nonwoven layers are put below the substrate 212 in the garment 200, and then more nonwovens are put on top of the absorbent mass 220, to hold the absorbent mass 220 in place.

Next, various other cuts and adhesive tabs are added while the garment 200 is still in "roll" form, including various alterations to make the garment 200 fit human anatomy. The last manufacturing step for creating a properly layered garment 200 is cut it to a pre-determined length and folded. This is important because the continuous strips of conductive ink (electrodes 204) are then completely encapsulated within the garment 200. At a top and bottom edge where the garment 200 is cut at the end of the manufacturing process, there is a thin nonwoven material on top of the electrode 204, the pre-printed poly film (substrate) 212, and perhaps (optionally) another nonwoven material underneath. This is the composite through which a conductive connection is made.

Within the embodiments of the garment 200 shown in e.g. FIG. 2B, the electrodes 204 are shown extending all the way to the edge of the substrate 212. However, this is for example only, for clarity and ease of illustration, but should not be considered limiting. It is not necessary that the electrodes 204 always be positioned this way.

A plurality of types of conductive inks 500 are printed onto a poly film (substrate) 212, which afterwards is referred to as a "pre-printed poly" film or substrate 212. These conductive inks 500 are used in creating the electrodes 204 and can be formed using a variety of methods, a non-limiting example being shown in FIG. 2D.

As will be discussed in more detail herein, the materials in the conductive inks 500 can comprise metals, carbon compounds in various concentrations, graphite compounds in various concentrations, or any material that will conduct electricity in a dry or wetted condition. The conductive inks 500 may be used for various types of printing, paint, thread, or forming film made of various materials, etc. The conductive inks 500 may also be blended with non-conductors for deposition, storage, handling, and improved durability. An insulating layer may be used with the conductive materials. Hydrophilic and hydroscopic materials such as cellulose may be added to improve detection characteristics of the conductive element. Dissimilar materials may also be used to obtain a response different from those obtained from a single material type.

At some point, perhaps immediately, but more likely later, and perhaps in a different geographic location entirely, the pre-printed poly film (substrate) 212 is eventually included within a manufacturing process of a garment 200. The width of the pre-printed poly film or substrate 212 can be e.g. 40-50", but the embodiments herein are capable of printing multiple widths at once. As shown for example in FIGS. 2A-2B, the electrodes (AKA conductive strips) 204 are printed in a direction parallel to the movement of the garment through the printing machine direction, and set up to be continuous (uninterrupted).

The electrodes 204 may be ¼" wide and 2" apart, but this is an example only and should not be considered limiting. The pre-printed poly film 212 is trimmed to the exact width used in the garment 200, and is then delivered to the garment manufacturing machine 112. As such, the garment manufacturing machine 112 incorporates the pre-printed poly film 212 as a feeder component, similarly to how that machine 112 might incorporate the plain "poly" that is conventionally used in garment products.

In an example embodiment, the pre-printed poly film (substrate) 212 is configured to a predetermined width which conforms to a width within the garment 200 being manufactured. The garment-manufacturing machine 112 can use multiple widths simultaneously. In an embodiment, it is possible to arrange the electrodes 204 to be parallel to a direction of the garment-manufacturing machine 112, although this arrangement is not mandatory. The garment-manufacturing machine 112 continuously produces the garments 200.

As stated, FIG. 2B shows a parallel pattern that is integrated with a garment 200 in a continuous roll method. However, despite what is shown in FIG. 2B, alignment of the substrate 212 is not required to occur only along the direction of manufacture (direction of rolling).

The sensor elements (electrodes 204) are conductive elements which may have either a positive or negative response to moisture. For example, resistance of the electrodes 204 may increase when exposed to moisture, or may decrease. Both DC and AC measurements or other forms of applied voltage, including cyclic voltammetry, over both positive and negative voltages may be made to detect the presence of moisture or the properties and components of the moisture.

The electrodes 204 may be deposited onto the substrate 212 using one or more of rotogravure, flexographic printer (as mentioned), ink jet, offset, screen, extrusion, or xerography printing methods. The electrodes 204 may be made also be made of a material that is placed on, in, or through the substrate 212. Examples of the latter are conductive tape, thread, or wire.

Figure 2C:
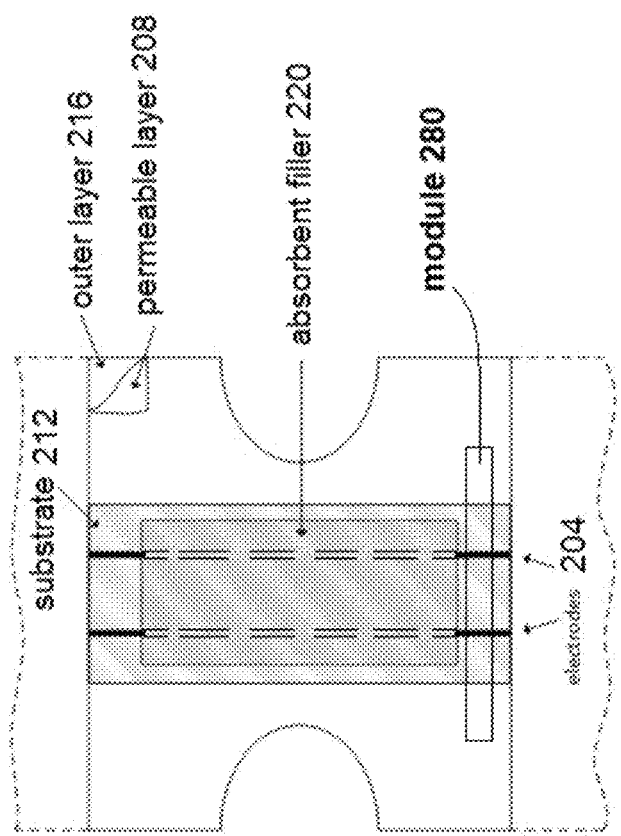
FIG. 2C shows a sensor module attached to the garment shown in FIGS. 2A and 2B.
Figure 2D:
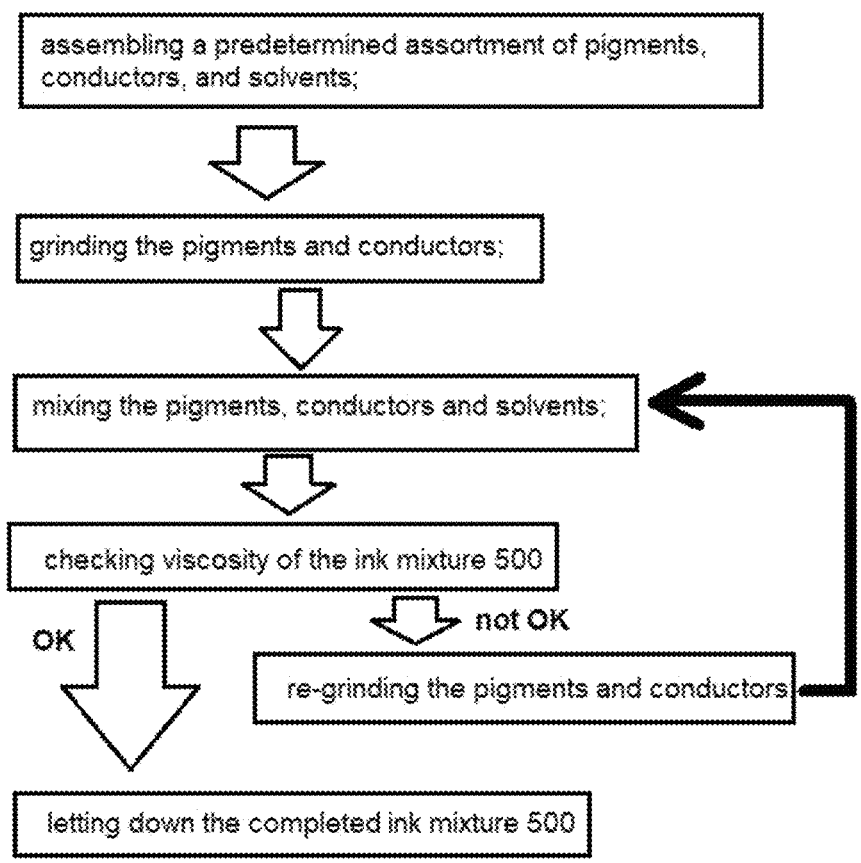
FIG. 2D shows an example method of manufacture.
Figure 3:
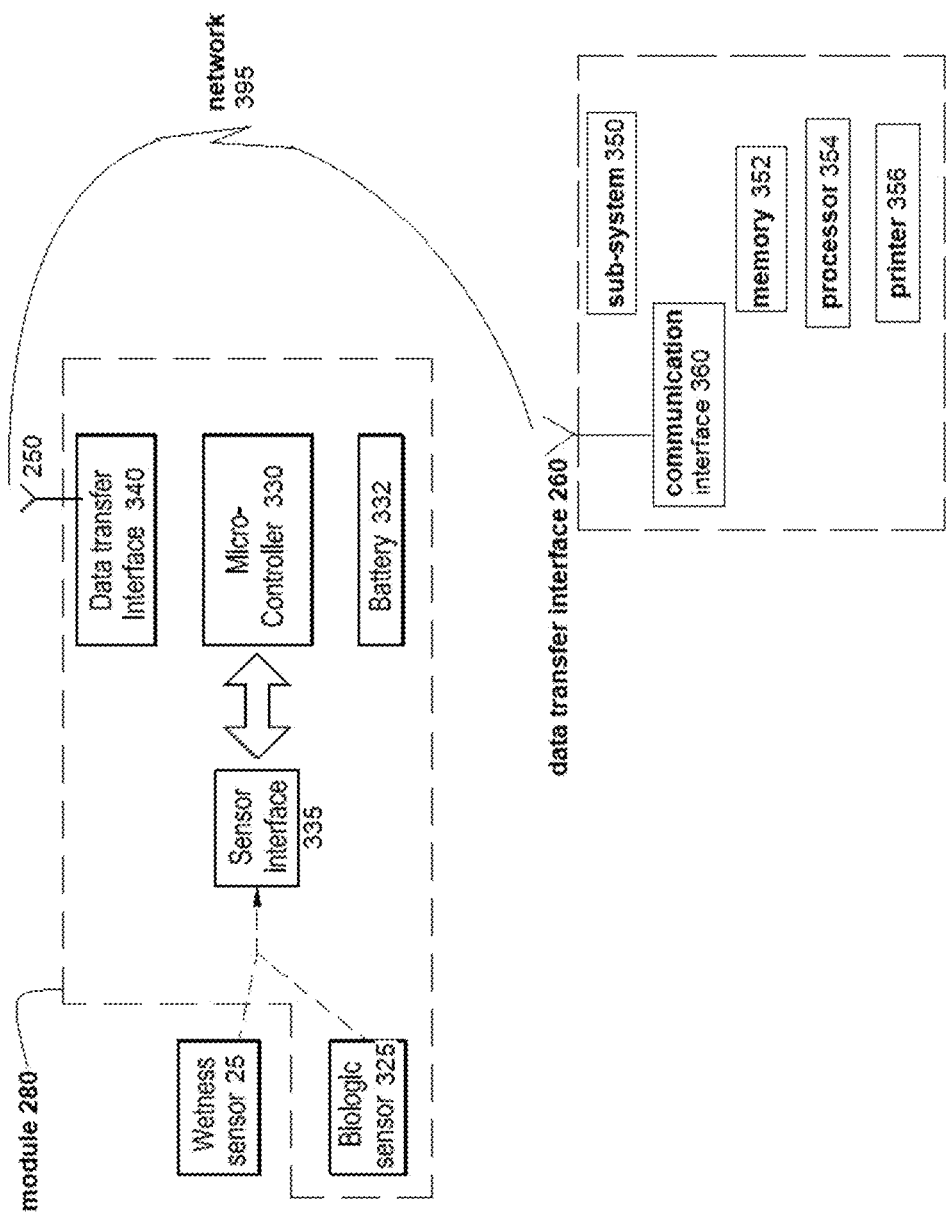
FIG. 3 shows detail of a sensor module.

FIG. 3 is a block diagram that incorporates some components of FIGS. 2A-2C in relation to other optional system components. The tag 200 communicates with either or both of wetness sensor 25 and biologic sensor 325, via a sensor interface within the tag. Signal transmission is also accomplished through microcontroller 330, which accepts sensor data indicative of the condition of a patient. Microcontroller 330 then relays such data to data transfer interface 340 which can be coupled to the antenna 250, for transmitting the signals to a separate data storage and processing sub-system 350 having an antenna 260 as well its own communications interface 360 for handling incoming and outgoing signals.

The module 280 can utilize any of a number of various communications protocols that have been described herein through either a wireless connection or wired means. In some embodiments, the sub-system 350 is equipped with memory 352, processor 354, and printer 356. Memory can be configured as either volatile or non-volatile memory, and includes in non-limiting fashion random-access memory (RAM), programmable read-only memory (PROM), flash memory, and other forms of database storage as well as any of a number of database management software tools for searching as would be typical for use with an electronic health record. Connection over the network 395 is optionally a public network using standard broadband transmission connected to various devices in multiple facilities and locations. Alternatively, network 395 is a private network of devices and clients linked over a local area network over a dedicated network connection.

In an embodiment, the processor 354 can be used for interpreting, sorting, and aggregating the received data. For example, machine-readable program instructions stored on processor 354 may be configured to interpret a "1" value to represent a wet or soiled brief, while a "0" value is interpreted to represent that no void event has occurred since a most recent changing. Each tag 200 has a unique identifier that enables the system to associate the information to the particular patient with that tag.

Figure 4A:
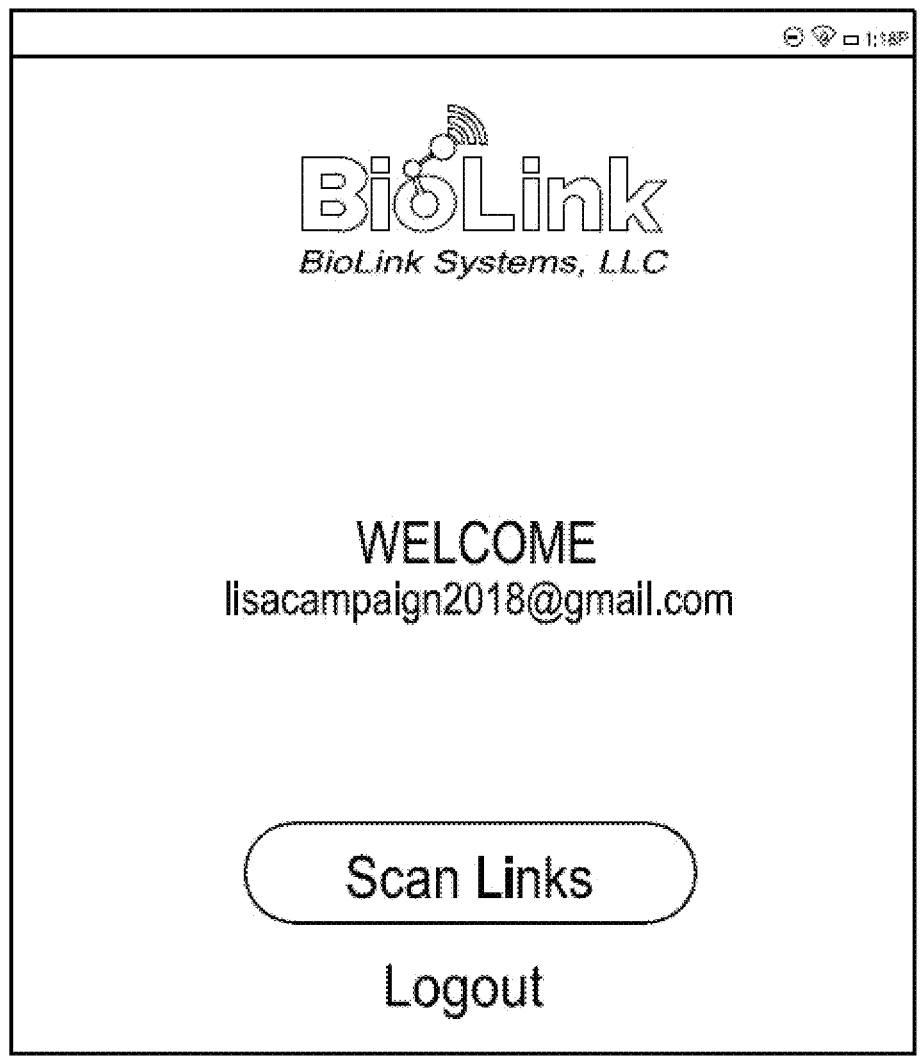
FIG. 4A shows a first of a plurality of mobile GUIs used within the embodiments herein.
Figure 4B:
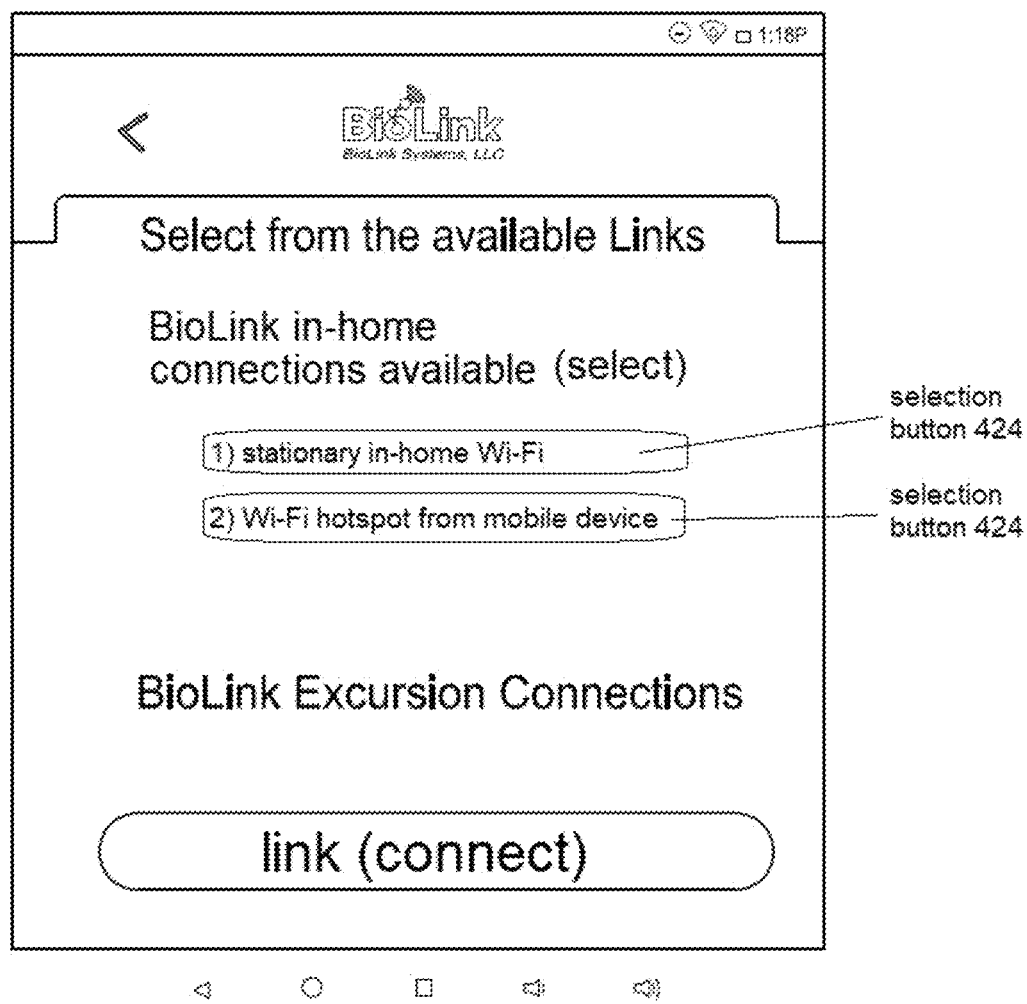
FIG. 4B shows a second of a plurality of mobile GUIs used within the embodiments herein.
Figure 4C:
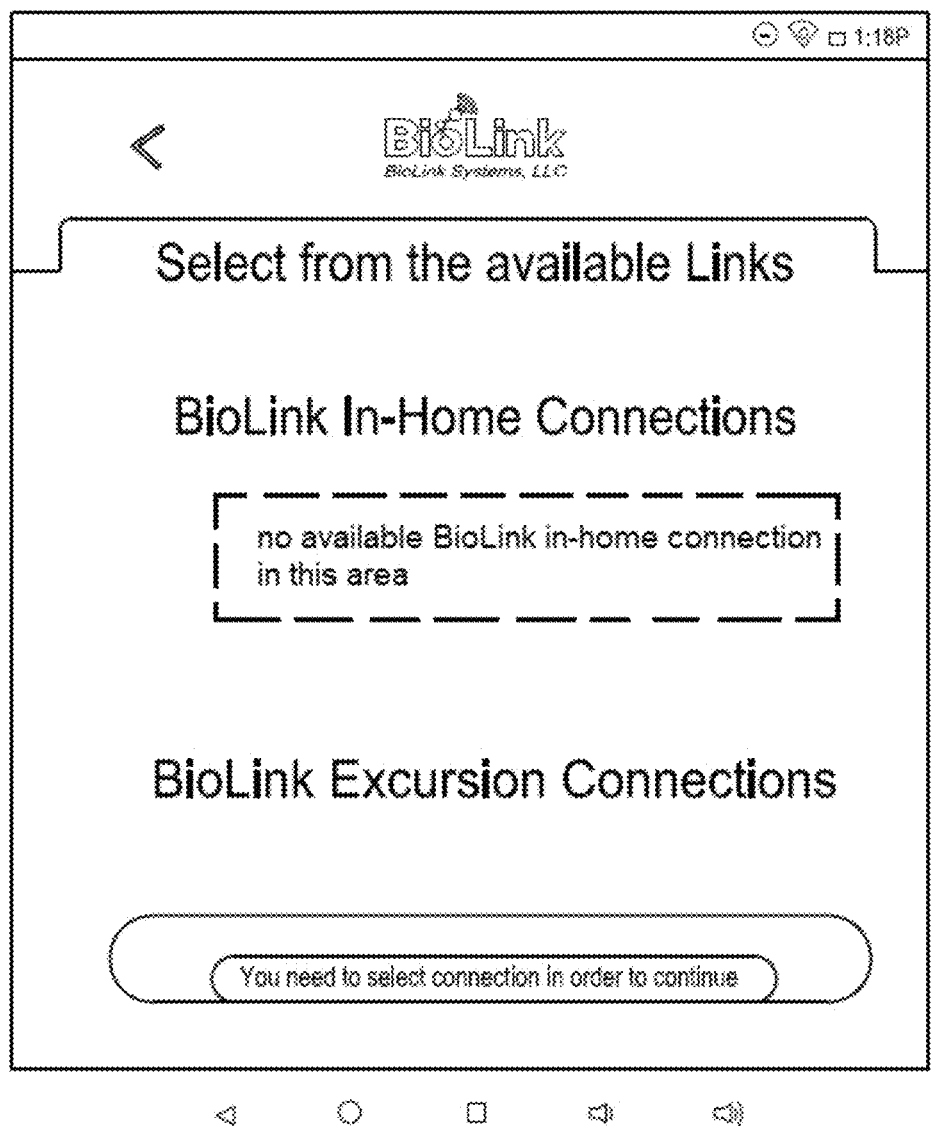
FIGS. 4C-4D show third and fourth of a plurality of mobile GUIs used within the embodiments herein.
Figure 4D:
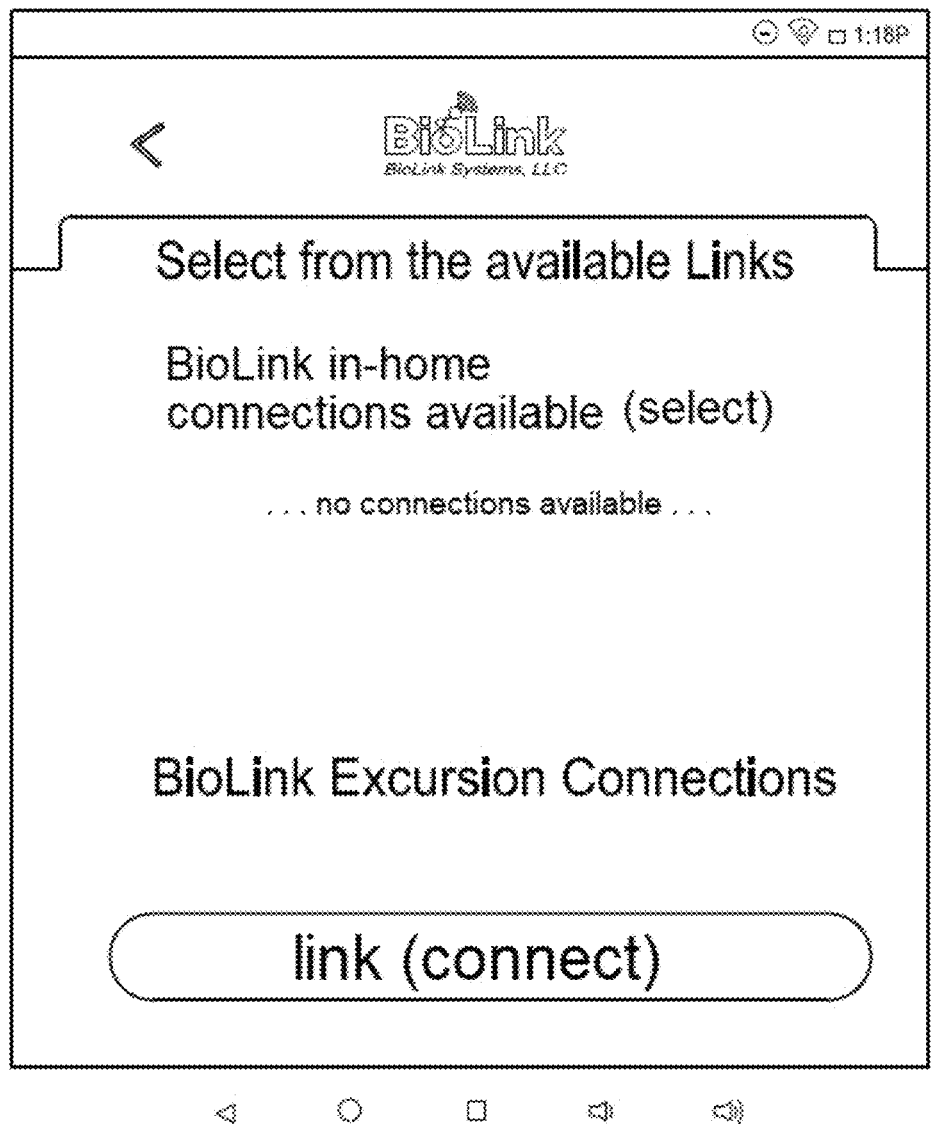

FIGS. 4A-4D show example non-limiting GUIs within an example mobile app, generally used for in-home non-institutional purposes. The bio-information sent to the GUIs shown in FIGS. 4A-4C comes from the module 280 (FIG. 2C). FIG. 4A shows an introductory screen, and FIG. 4B shows how a user will be advanced to selecting some type of in-home computer network location, two examples of which are "stationary in-home Wi-Fi" and "Wi-Fi hotspot from a mobile device". Thus, within FIG. 4B, the "locations" are not physical locations but network locations. Users can only connect to one location at a time. If no computer-network locations are available, the GUI will resemble that shown within FIG. 4D. Conversely, all available computer-network locations will be marked with a selection button 424. FIG. 4C shows an example message that comes up when a user has not selected any network. FIG. 4D shows an example GUI showing an instance where no computer-network locations are available.

In an embodiment, the processing sub-system 350 can be a type of caregiver workstation such as is typically used in a nursing home or residential facility. However, the data transfer interface 340 can also be contained in a mobile device such as what his shown in FIGS. 4A, 4B, 4C, and 4D.

Figure 4E:
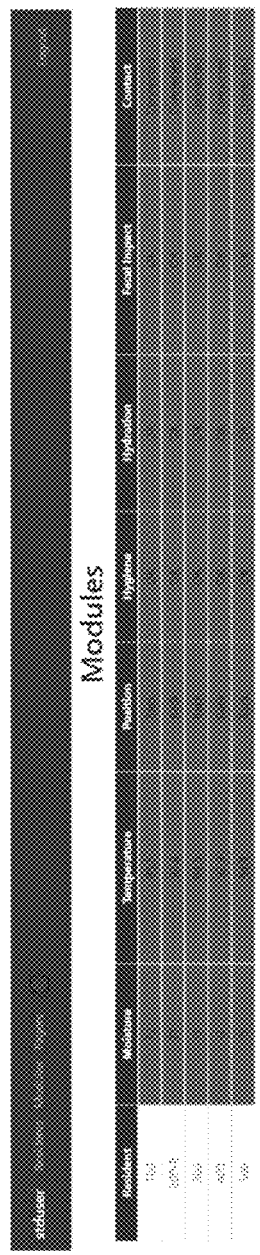
FIG. 4E shows a desktop GUI used within the embodiments herein.

Again, the embodiments herein serve both at-home non-professional caregivers (e.g. relatives) as well as professional caregivers in e.g. hospitals, nursing homes, and other institutions. Accordingly, FIG. 4E shows a GUI for software used by a non-home fully professional environment, such as a nursing home, hospital, or other type of institution. In an embodiment, the processing sub-system 350 works with the GUI used by a non-home fully professional environment shown in FIG. 4E.

The substrate 212 can be a paper, fiber, a plastic film, or other material that can form a 'fil' (not a spelling error) of mesh. The substrate 212 can be smooth, or contain embossed features to improve deposition of materials. Embossing or patterning of the substrate can be used to improve resistance to broken conductive paths of the electrode 204.

Optionally, tracked information such as that shown in FIG. 4E (and elsewhere) is aggregated and further processed to provide patient-specific information on average interval between voids, for example based upon the last ten (10) such events, or any suitable sample size as desired. This can prove helpful in predicting future events or establishing a pattern of knowing when to look for the next such event. Though not shown in FIG. 4E, other information tracked and listed may include the current status of the patient: whether "dry" (no voids since most recent changing), or "wetness detected," including an indication of the duration since this finding occurred. There are various ways to depict the status as can be chosen by the user, for example as visual piece of information or an icon with a bubble darkened next to one of several optional levels to indicate the status.

Where the GUIs of FIGS. 4B and 4C say "Excursion mode", that refers to a Bluetooth connection to a mobile device 280. In that embodiment, the module 280 and the mobile device or tablet (and displayed by the GUIs) are the only hardware. The module 280 advertises via Bluetooth and the mobile device or tablet picks up that advertisement if within range. Simplicity is the advantage here, but the limited range of BlueTooth® (e.g. 30 feet) can be somewhat of a disadvantage. Thus, the "excursion" of FIGS. 4B and 4C can be a distant excursion, but the distance between the module 280 and whichever type of mobile device should not exceed 30 feet (BlueTooth® range). The word "excursion" arises from the idea of a relative or loved one taking a resident out of a nursing home or other facility for e.g. a mini-vacation, e.g. excursion.

FIGS. 8A and 8B show flowcharts of a method of assembling and testing a garment 200. Regardless of the specific form of the resulting garment 200, all embodiments discussed herein will be manufactured using some variation of one or more electrodes 204 in the form of conductive strips. All embodiments discussed herein will be disposable. In other words, it is intended that there will be no laundering of the garment 200. Whether the garment 200 is in the incontinence diaper format or the briefs (underwear) format, the garment 200 will be single-use, disposable, and not intended to be laundered or re-used.

Another advantage of the embodiments herein is that it is possible, in some embodiments, to reduce the thickness of the absorbent filler 220. In some existing garments, the amount of absorbent filler is sometimes increased in order to minimize discomfort on the wearer if their diaper remains unchanged for a while. In contrast, the embodiment herein overcome this because when the embodiments herein are properly implemented, the active, real-time monitoring for wetness that occurs will limit how long a person will have to wear a wet garment/diaper, so that extra filler 220 is un-necessary. This in turn can reduce the cost of the garment 200.

In an embodiment, moisture within the garment 200 is sensed by measuring the resistance between two conductive paths. When moisture is present between these paths, the resistance can, for example, increase or decrease. The value of resistance can be, for example, a function of the sheet resistance of the parallel electrodes 204, the distance from the measurement connection of the module 280 to the moisture, the conductivity of the moisture applied across the conducting paths, and for some material, the voltage applied to measure the resistance.

Figure 7:
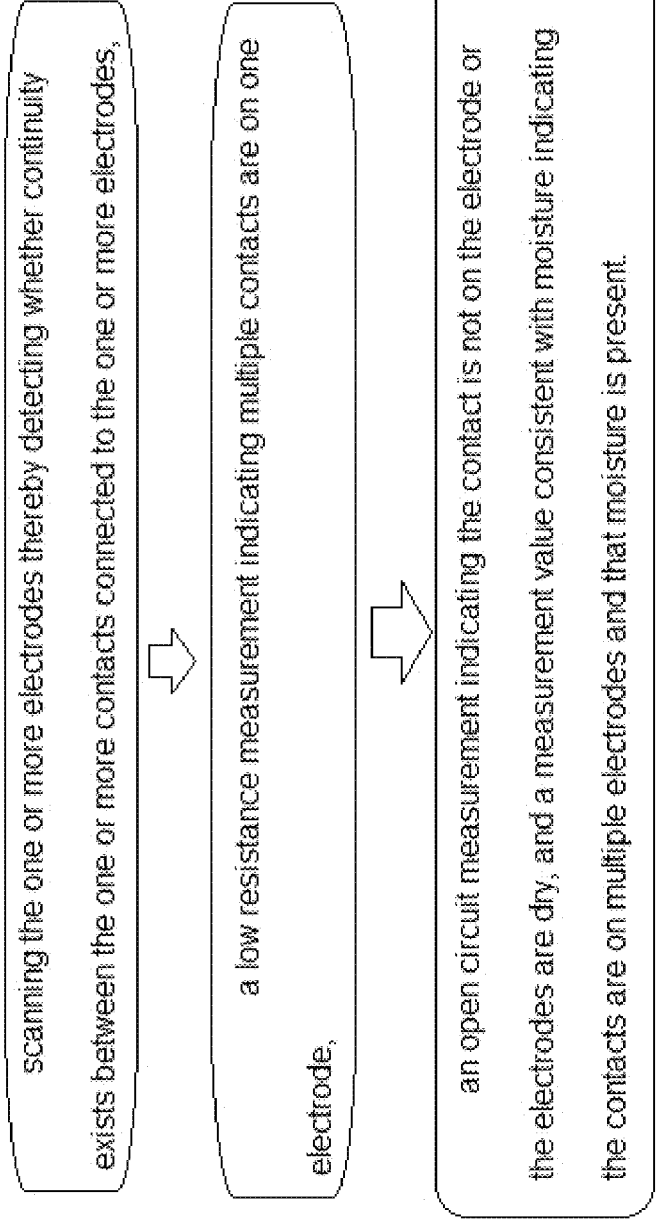
FIG. 7 is a flowchart showing a method of using the embodiments.

FIG. 7 shows a flowchart of an example method of using and operating the garment 200. Although modules 280 are preferably reusable, it is anticipated that modules 280 will need to be replaced eventually. Also, it is possible for modules 280 to become lost or misplaced. Thus, it will often be useful to track the status of the module 280 itself. In some embodiments, this is accomplished by recording the date a module 280 was first put into use and otherwise implemented. This is accomplished by assigning a unique identifier to a particular module 280 such as but not limited to a MAC address. From that point, all data associated with that identifier is linked to the particular module 280.

A typical life cycle of a module 280 can be determined and used for calculating and showing how many days until replacement will be needed. It is also possible to track information such as the length of time since the battery was last changed or replaced. The modules 280 can also be equipped with a function capable of responding to a query sent via Bluetooth, programmed to be directed to a specific module 280 based on its identifier, in which the module 280 associated with the identifier emits an audible noise in response to the query.

End Overview, Begin Ink-Specific Sections

The above was intended to provide a type of overview and explanation of the overall embodiments, where those embodiments fit into the world, and how these embodiments will be commercialized and implemented. However, the remainder of this disclosure will be limited to the composition, manufacture, and testing of the conductive inks themselves, as well as the manufacturing and shipping processes associated therewith.

The embodiments herein contribute to production of a printed circuit at extremely low cost, so that a disposable garment can be produced competitively. There are plenty of existing conductive inks and processes to make and print such garments, but these are overly costly.

Manufacturing the Ink

In all embodiments herein, it is important to remember that the ink developer is not the same as the printing personnel. These are almost always two separate service providers, with separate locations. The embodiments herein strive to facilitate these two separate entities working well together. Further, there can be different film producers and different garment manufacturers. Each will have unique process variables that the embodiments herein need to accommodate.

Figure 5A:
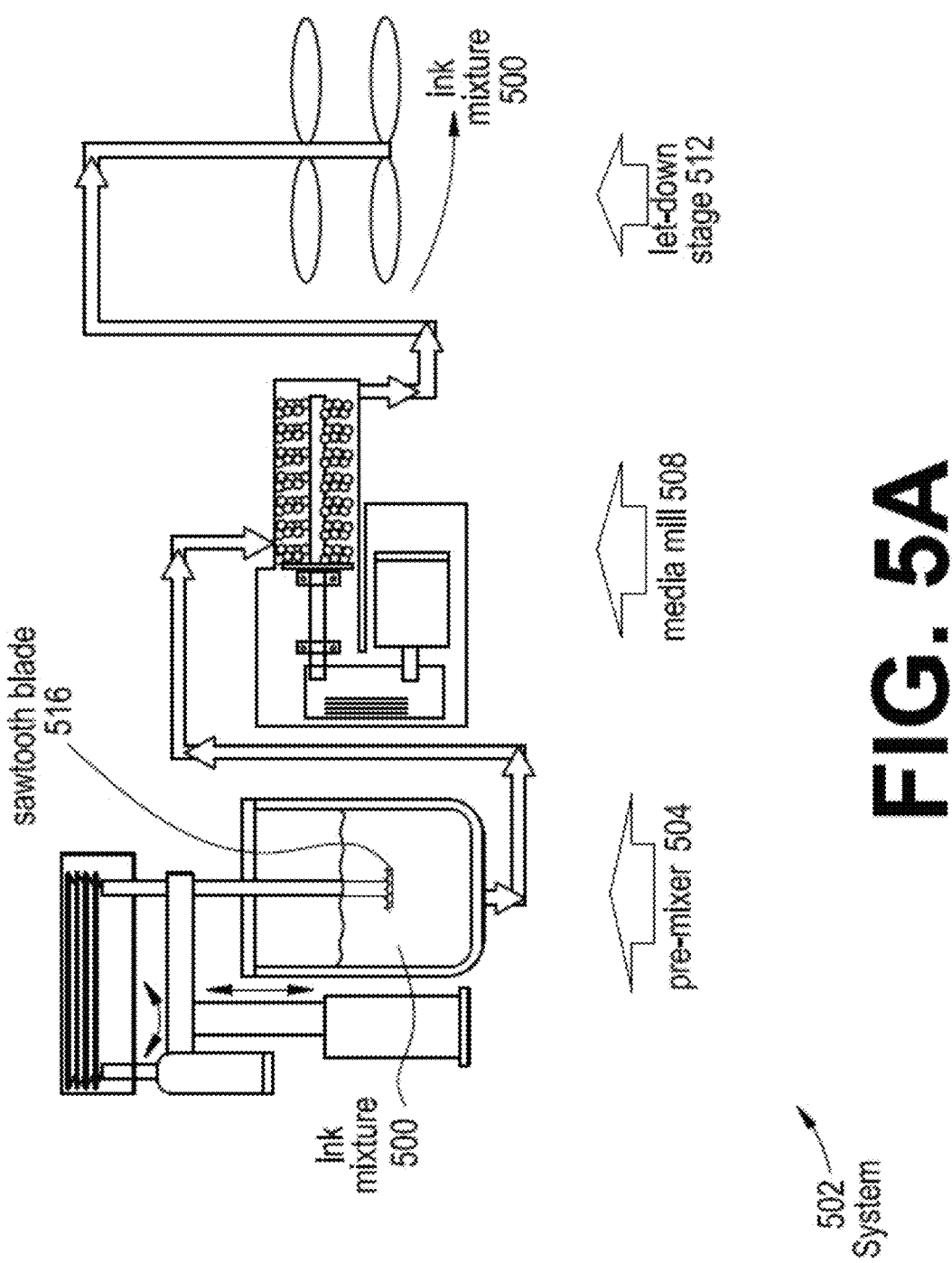
FIGS. 5A, 5B, 5D, and 5E show example disperser arrangements.

As shown in FIG. 5A, the ink mixture 500 begins its manufacturing process by mixing carbon, graphite, and solvents in a system 502. This mixing may occur in a Cowles disperser (where Cowles is written with an upper-case C because of being a term of art). It is important that the conductive portions (e.g. carbon, graphite) be evenly and universally dispersed, because an even dispersal means the conductivity of the resulting conductive strip (electrode) 204 will be even, consistent, and reliable.

The embodiments of ink mixture 500 described herein comprise a blend of different conductive pigments, including but not limited to carbon black and graphite. These embodiments must be grinded until below 6.5 Microns (measured using e.g. a Hegman device). For the solvents, an embodiment uses a blend of normal propyl acetate and normal propyl alcohol. As shown in FIG. 5A, this ink mixture 500 is passed from the pre-mixer 504 to the media mill 508 and to a let-down stage 512. The ink mixture 500 should arrives to the media mill 508 only after a thorough Cowles agitation (AKA a dispersal made using a Cowles blade). In an embodiment, the pre-mixer 504 may contains a Cowles disperser and a sawtooth blade 516 (e.g. FIG. 5C). For convenient references, the pre-mixer 504 may sometimes be referred to as a Cowles disperser 504.

Being at a sub 6.5 Micron level improves conductivity. In an embodiment, the ink mixture 500 is printed on LDPE (Low-Density, PolyEthylene) stock. However, in working with different printers as service providers, it is important to be consistent with the LDPE, as the existence of other elements that were not present in typical LDPE stock, including but not limited to micro-embossing, can interfere with print-quality and introduce unexpected and uncontrollable results. In addition to micro-embossing, there can be variations in a resin content of the film, and also variations in treatment of the finished film (e.g. flame-treating). Thus, this provides another reasons why controlling consistency of the LDPE stock is an important part of the embodiments herein.

The impellers within a Cowles disperser are sometimes referred to as Cowles blades. As shown in FIG. 5C, the Cowles blades can have a sawtooth profile 516 that is rotated at a high RPM to create the shear force to break down pigment agglomerates. For optimum dispersion results, the diameter of the Cowles blade should be between 50%-75% of the inside diameter of the container vessel 528, sometimes known as a squat tank 528 (e.g. FIG. 5E).

If not using a Cowles disperser, the resulting solution would not have consistent viscosity even, and could even resemble sludge which would not conduct well. The embodiments herein are effective partly due to the conductive nature of the raw materials, which include specially blended carbons and graphites. However, the process does not end there, this blend of the ink mixture 500 must also be the correct particle size, and also must be dispersed correctly. All pigments, when originally derived, have a tendency to want to come together, chunk up, agglomerate, and not be stable. Cowles dispersers 504 help overcome this tendency.

The embodiments herein take solids and create the ink mixture 500 to reduce grit, partly by grinding the solid particles to a point where the solid particles are at a sub-micron level and thus feel smooth to the touch. Ideally, the act of printing the ink mixture 500 should not yield any gritty substance or salt or residue. One way to do that is to force the ink mixture 500 through the media mill 508, which may be horizontal, but may also be non-horizontal.

The ink mixture 500 has to be dispersed properly, at the beginning of formation. This is generally achieved with the Cowles disperser 504. There can be many different kinds of blades within a Cowles disperser 504, including impeller blades, cut blades, and sawtooth blades. An example sawtooth blade is shown at least within FIGS. 5A, 5C, 5D, and 5E Next, it is desired to disperse the ink mixture 500. The solvent in this case would be a Normal propyl alcohol, Normal propyl acetate combination optimally at an 80%-20% proportion (Normal is spelled with an upper case 'N' due to being a chemistry Term of Art). Within the embodiments herein, drying speeds are an important consideration. Drying speeds will be dictated partly by the choice and proportion of solvents. A drying speed is going to be faster where the solvent has a higher amount of acetate content, and is going to be slower with less acetate content.

Figure 5B:
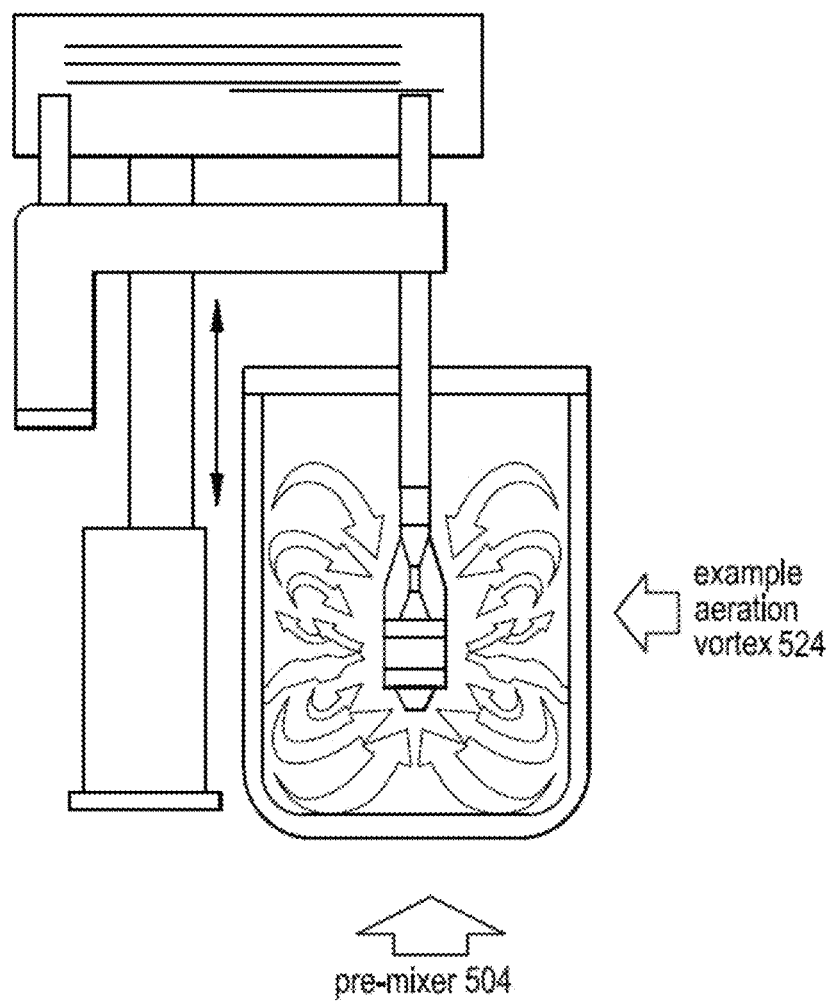
Figure 5C:
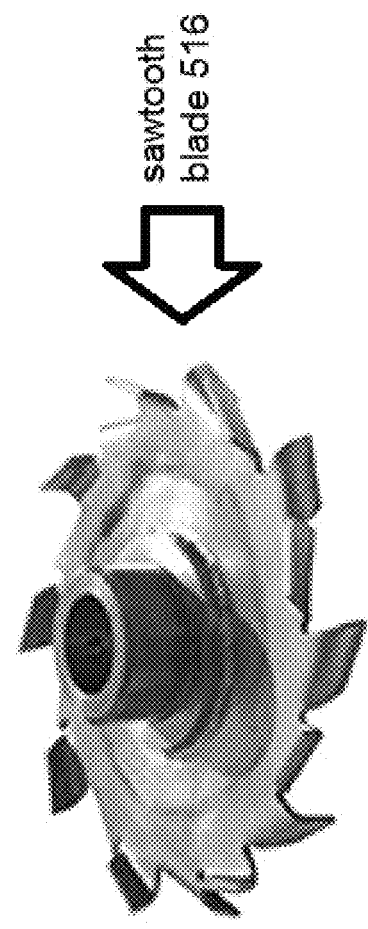
FIG. 5C show example disperser arrangements.
Figure 5D:
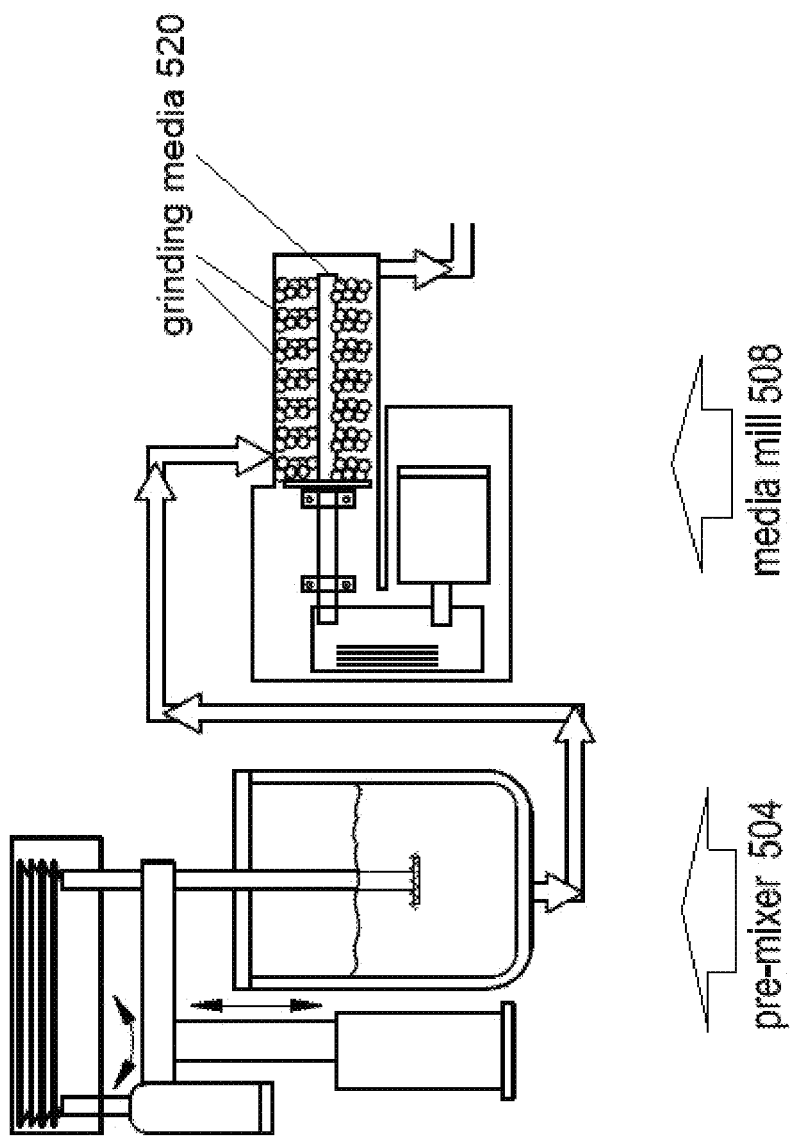
Figure 5E:
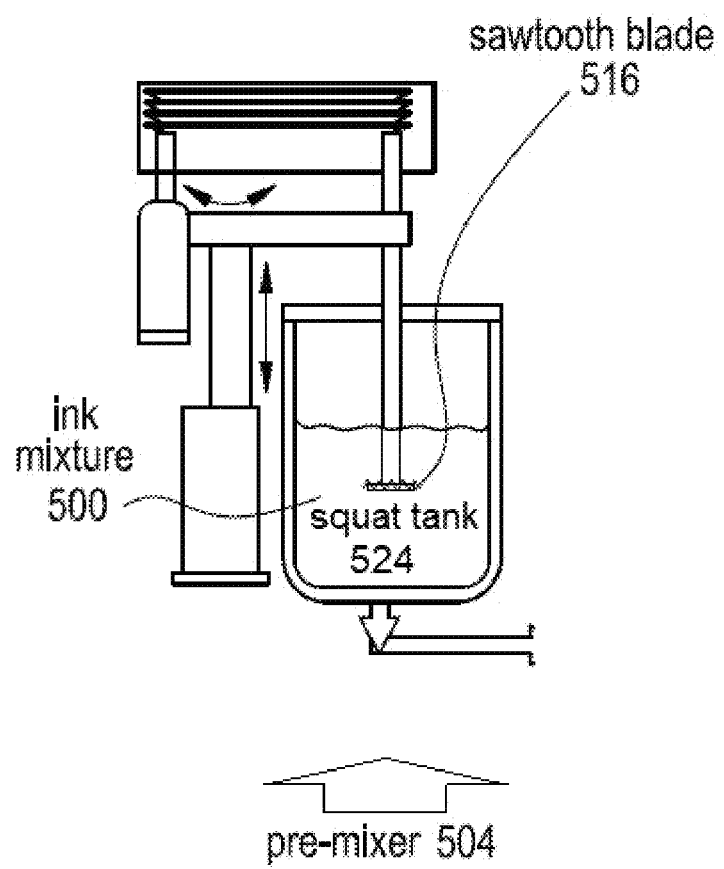

All solvents would be included in the disperser tub or tank 528, examples of which are shown in FIGS. 5A, 5B, 5D, and 5E. Generally, it is desired to have a ratio where the Cowles blade size is ⅓ the size of the tank vessel 528. It is also helpful to have that Cowles blade be about half the diameter of the tank vessel (tub) 528, measuring from the bottom of the tub 528. This ensures creation of a vortex 524 below that blade that will take the solid materials and move them almost in what looks like an hourglass (or Kama Sutra) vortex formation 524. An example vortex 524 is shown in FIG. 5B.

During initial formation of the ink mixture 500, a high viscosity is used to induce shear for dispersion. In general, at low viscosity, little\minimal shear is achieved. To reach effective dispersion, vortexing (aeration) is necessary. Vortexing ensures that no pigment is trapped in the vessel 528 which is not getting circulated. If the Cowles blades are too high, pigment can be trapped right below the Cowles blades. In contrast, if the blades are properly located, the vortex 524 keeps the ink mixture 500 moving and non-trapped. Thus, the arrangement described herein ensures all solids, when added to the liquid (solvent), are being forced into that Cowles blade (e.g. sawtooth 516) and then are dispersed correctly into the ink mixture 500.

The importance of proper dispersion has a parallel with making mayonnaise. It's not sufficient to merely mix egg whites and oil. In doing so, one may have the ingredients to make mayonnaise, but just taking egg whites and oil and smacking the combination around with a fork, that may result in a glob of nothing. Conversely, when oil is properly dispersed within those egg whites, only then can mayonnaise be produced.

Thus, it's important that the Cowles blade is correctly chosen, the position of that blade is correctly chosen, and the solids are added to the liquid solvent at a predetermined pace chosen to not overload the system 502. This is the only way to ensure that everything disperses properly. Then, after that dispersion is made, the Cowles mixer (disperser) 504 with a sawtooth blade 516 will grind, that is, reduce the micron size of the resulting solution (measured e.g. on a Hegman scale).

As stated, it's important that solids are being added to liquids (solvents) at a moderate pace. It's not an exact science with a stopwatch, but suitable monitoring is necessary to avoid overloading the Cowles disperser. Additionally, it is desired for the Cowles disperser 504 to be able to disperse appropriately when set up properly, for example with a dispersant blade that is ⅓ the size of the tub.

However, as shown in FIG. 5A, the Cowles mixer (disperser) 504 is only part of the process, and does not do all of the work of mixing the ink mixture 500. One example which proves this out is titanium, which is an easy pigment to disperse and grind. It is possible to grind dry titanium pigment into a solution using only a Cowles disperser 504 and do quite well. However, titanium is about the only solid that works this way. Most other solids require further processing.

So, step one is dispersing the solids as well as possible, but this still is only the beginning of grinding product and the reduction of the solids within the ink mixture 500 (hence the name pre-mixer 504). This now has some of the work so that the ink mixture 500 done in the pre-mixer 504 that can be pumped into a media mill 508, as shown in FIGS. 5A and 5D.

The media mill 508 contains grinding media 520 which could be steel beads, glass beads, or some kind of synthetic bead, depending on the size of particle that desired. Other non-bead shapes can also be used for the grinding media 520. In an embodiment, a bead size might be somewhere around 10 times the desired end-size of the pigment (solids) being grinded, however that is a suggestion only, and not a strict limit. In essence what a grinding media mill 508 will do is push a dispersed solution through a small tubular-like structure. The media mill 508 can be very helpful in achieving<6.5 µm size.

In the media mill 508, through high pressure and shear force, liquid containing pigment is driven through all the grinding media 520 and then this media 520 rubs together and grinds the pigment down to a size that is acceptable. As stated, the embodiments herein strive for, in a non-limiting example, a maximum of 6.5 microns on the Hegman scale, if not lower. Driving pigments (solids) through the media mill 508 is an important part of the processes herein. If the particle size is not properly controlled and isn't consistent, the desired conductivity may not be achieved, or may be inconsistent. The embodiments herein are not limited strictly to use of a horizontal media mill 508, as long as the end-result is consistent and controllable particle size. For example, a media mill 508 could be used that is not entirely horizontal.

Many factors in grinding exist including striving for optimum size that is most suitable for the conductive components of the ink mixture 500. One factor could be to calibrate pigment-size to a specific threshold so as to achieve optimum carry-ability of that pigment. Within the embodiments herein, those aspects are relevant for the ink mixture 500, but it is also important that the grinding process brings the pigments to a size that will allow the ink mixture 500 to be conductive.

Figure 6A:
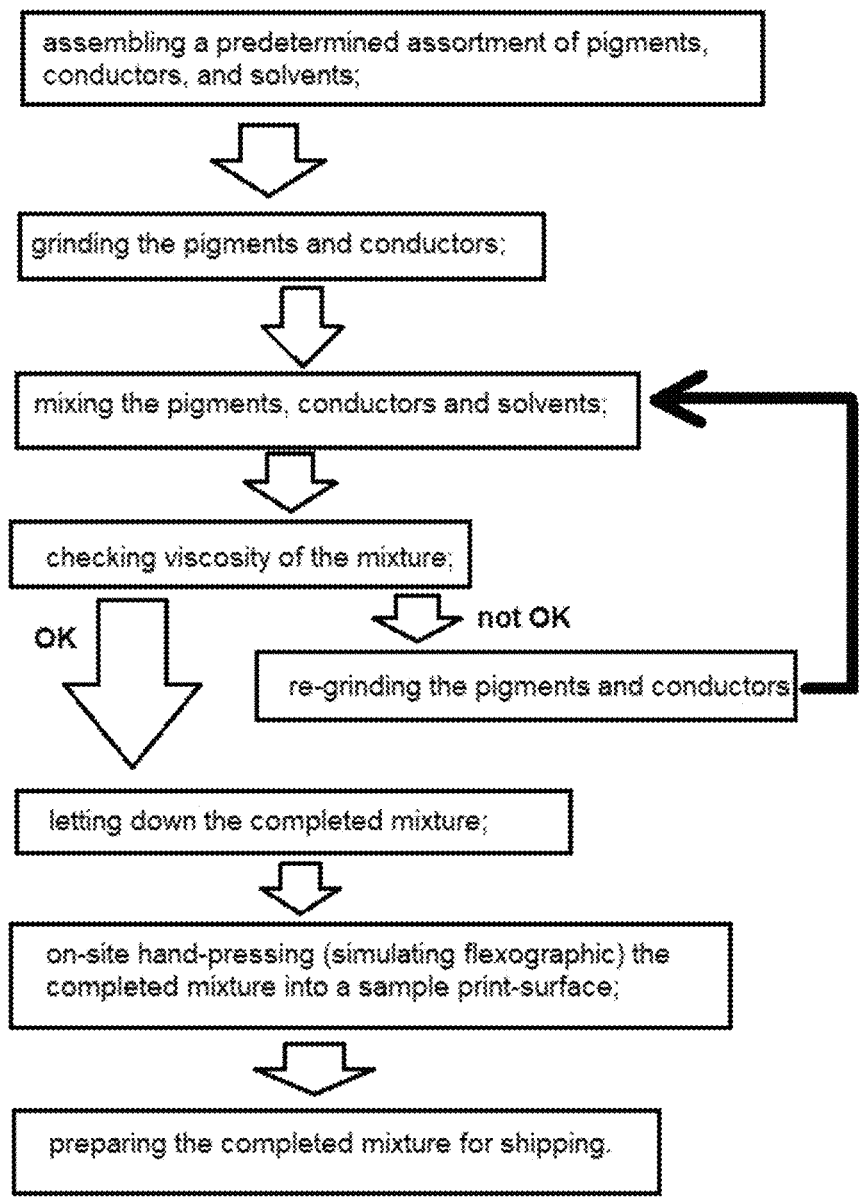
FIGS. 6A, 6B, and 6C show methods of testing the embodiments.

Various of the manufacturing steps described herein are summarized in FIG. 6A, which is a summary-only and thus non-limiting.

As stated, the solvents used in the ink mixture 500 can include Normal propyl alcohol and Normal propyl acetate.

However, another possible solvent could be glycol ether PNP, which would be a slow-drying solvent. As stated earlier, acetate is going to speed up drying. But usage of acetate must be kept below specific predetermined limits, e.g. 20%. More acetate than 20% could result in mechanical problems with the photopolymer plates and rubber rollers and other items in the flexographic printing equipment.

Glycol ether PNP would be a solvent that could be used to slow the drying of the ink mixture 500. A specific embodiment of the ink mixture 500 strives to print fast and put multiple layers on top of each other. As such, this specific embodiment will strive to be as fast drying as possible, to avoid picking or merging of the two layers or things that could potentially cause issues. However, it is also possible to have other embodiments in which slower drying is an advantage.

As stated, an embodiment of the ink mixture 500 is as fast drying as possible, to avoid picking or merging of the two layers or things that could potentially cause issues. At least two separate embodiments of fast-drying versions exist. In one embodiment, a substrate is run through a printing press where a first run of the ink mixture 500 is applied, and then completely re-passed through that same press where another run of the ink mixture 500 is applied to the same surface of the same substrate. While not optimal, there may be circumstances in which a single press is all that is available. One example might be where there is only one "sleeve" (the printing plate that slips on a circular roller within the flexo-printer), so that its necessary to double-pass (double-bump) the ink mixture 500.

It is possible to run garments 500 through the same printing press twice, but it's also possible to use two print stations, thus running through a press only once. Accordingly, a second embodiment may use two print decks, so when the ink mixture 500 goes to the printer, printer deck A will print a line, and then printer deck B will print a line. In an embodiment, it is suitable to put enough space between the decks such that the first layer is dry before applying a second layer. Solvent-based inks are better for this because of drying more quickly. Using 2 decks, however, is the preferred method. The option of using two passes on a single press is less likely to be used, but circumstances arise where there may be only a single plate available.

Any usage of flexographic ink will involve a vehicle, including resins carried by that vehicle. Within the embodiments herein, the vehicle that will carry those resins will likely be poly amide and nitrocellulose. In early iterations of the embodiments herein, the vehicle (e.g. the poly amide and nitrocellulose), was acting to insulate the pigment that's being carried within the ink mixture 500. The result was not making a common enough bridge for the conductivity to travel through the small volume ink strip 204 (e.g. FIG. 2).

Solvent systems often aren't conducive to flexographic printing because they melt the plates, swell rollers, have other negative effects, and may be contained in a very aggressive solvent. As part of an experimentation process, applicant made a print of that material on Low Density PolyEthlene (LDPE) and it was suitably conductive. The graphite content was bridging these insulation gaps, thereby allowing electricity to jump from carbon to carbon to carbon, with the bridge of a graphite to make this jumping happen.

To make the ink mixture 500 more flexo-equipment-friendly, an embodiment takes the carbon and the graphite which are conductive co-components and locates them in a polyamine, nitrocellulose based flexographic solvent system. Alcohol and acetate will be the solvent that would run that would neutralize or liquify the ink in the conductive components.

Within the embodiments herein, the ink mixture 500 will comprise both solids and solvents, always adding up to 100%. As stated earlier, the solids percentage will be e.g. 33+/−3%, while the solvent percentages will be 64-70%.

For purposes of explanation of FIG. 5A, it will be assumed the grinding is satisfactory and various other conditions are fulfilled for the ink mixture 500. At that point, it would be suitable to flush ("let down") the ink mixture 500, at the let-down stage 512. At the state where this happens, the ink mixture 500 would be assumed to be finished, and where final quality checks will begin. These will start with viscosity, because if viscosity is off then something is wrong. Typically shipping out an ink mixture 500 measuring for example from 30-34 in a 2-Zahn. If the material is outside 30-34, there is likely a problem. On a hot day some solvent may be lost due to evaporation, but to address this, one can add a little bit more solvent back in. Also, one can verify this problem during solids-level checks as well. If solids are too high, then solvents must be too low. That can be occur to loss of solvents through evaporation.

Testing the Ink Mixture 500

Viscosity Testing

A Hegman gauge, sometimes referred to as a grind gauge or grindometer, is used to determine how finely ground are the particles of pigment (or other solid) in a dispersion. The Hegman gauge consists of a steel block with a series of very small parallel grooves machined into it. The grooves decrease in depth from one end of the block to the other, according to a scale stamped next to them.

A Hegman gauge is used by puddling a sample of mixture at the deep end of the gauge and drawing the ink mixture 500 down a flat edge along the grooves. The ink mixture 500 fills the grooves, and the location where a regular, significant dots in the mixture appears marks the coarsest-ground dispersed particles. The reading is taken from the scale marked next to the grooves, in dimensionless "Hegman units" and/or millimeters (mm) or micrometers (μm).

There are many ways to test viscosity of a fluid, one of which is using Zahn cups. Zahn cups exist in multiple sizes. Within the disclosures herein, a #2 Zahn cup will likely be used. Viscosity is often measured in units of Centipoise (cP), but Zahn cups do not measure this way, instead Zahn cups measure viscosity by time (in seconds). To facilitate low-cost manufacture, the embodiments herein will be measured by how long, how many seconds, a fluid will take to run through a #2 Zahn cup.

Next, within the embodiments herein, a "shipping viscosity" can be different than a "run-viscosity" (printing viscosity). Suitable finished product (finished embodiments of the ink mixture 500) can be shipped out which measures between 30-40 seconds in a #2 Zahn cup. Meanwhile, it may be recommended to be thin, for example in the range of 24 to 26 seconds on the printing press, to "run" appropriately. This difference is intentional. Some factors are printer-dependent. Further, some printers have pumps and machinery setups where the operators and service providers of the flexo-equipment prefer to run thicker ink, while others may need to run on the thinner side. It is a part of the embodiments herein to grant some autonomy to the local printer, who may have their preferences of how they go about completing tasks.

When making the ink mixture 500, typically a manufacturer will strive for 30 to 35 in a 2-Zahn, which is a standard range and most printers will typically want to print at 24-26 in a 2-Zahn. The reason that product is at shipped out at a slightly higher viscosity then what is the recommended range for the printer is due to possible solvents that are latent into the hosing or the equipment at the printing press. Most printer persons, if they know what they are doing, would like the ability to control their viscosity to their specific scenario rather than to have viscosity entirely controlled by the manufacturers. All parties involved would prefer to leave the end-printer with this flexibility.

To achieve this, within the embodiments herein, one possible run-viscosity would be a range of 24 to 26 seconds as determined by a #2 Zahn cup. Again, this is not shipping-viscosity, but instead run-viscosity, that is, the viscosity as the ink mixture 500 is poured into the flexographic equipment and "run" (printed).

Using a Zahn cup involves dipping the cup into a fluid, e.g. the ink mixture 500, and lifting the Zahn cup upwards at the stopwatch. There's a stream that comes out of the bottom of the cup, where the stream starts to break ½ inch from the bottom of the Zahn cup. The number of seconds to travel through that Zahn cup is directly proportional to the viscosity of the liquid contained therein. Zahn cups are convenient in the industry because on-site operators can check viscosity very quickly, with a reasonable degree of accuracy. Further, using a Zahn cup does not require extensive technical expertise. As stated, low-cost operator-friendly testing is preferred where possible.

Figure 6B:
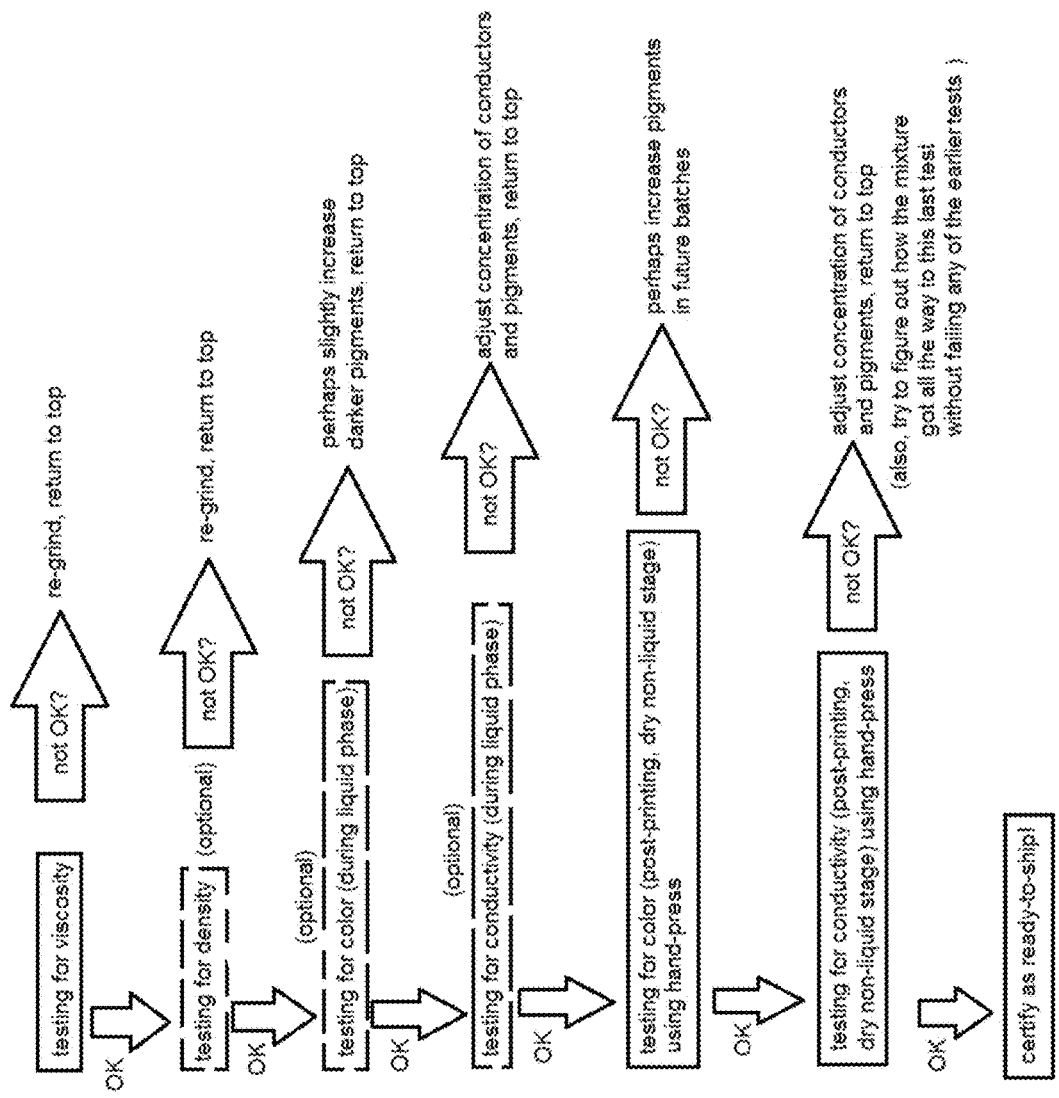
Figure 6C:
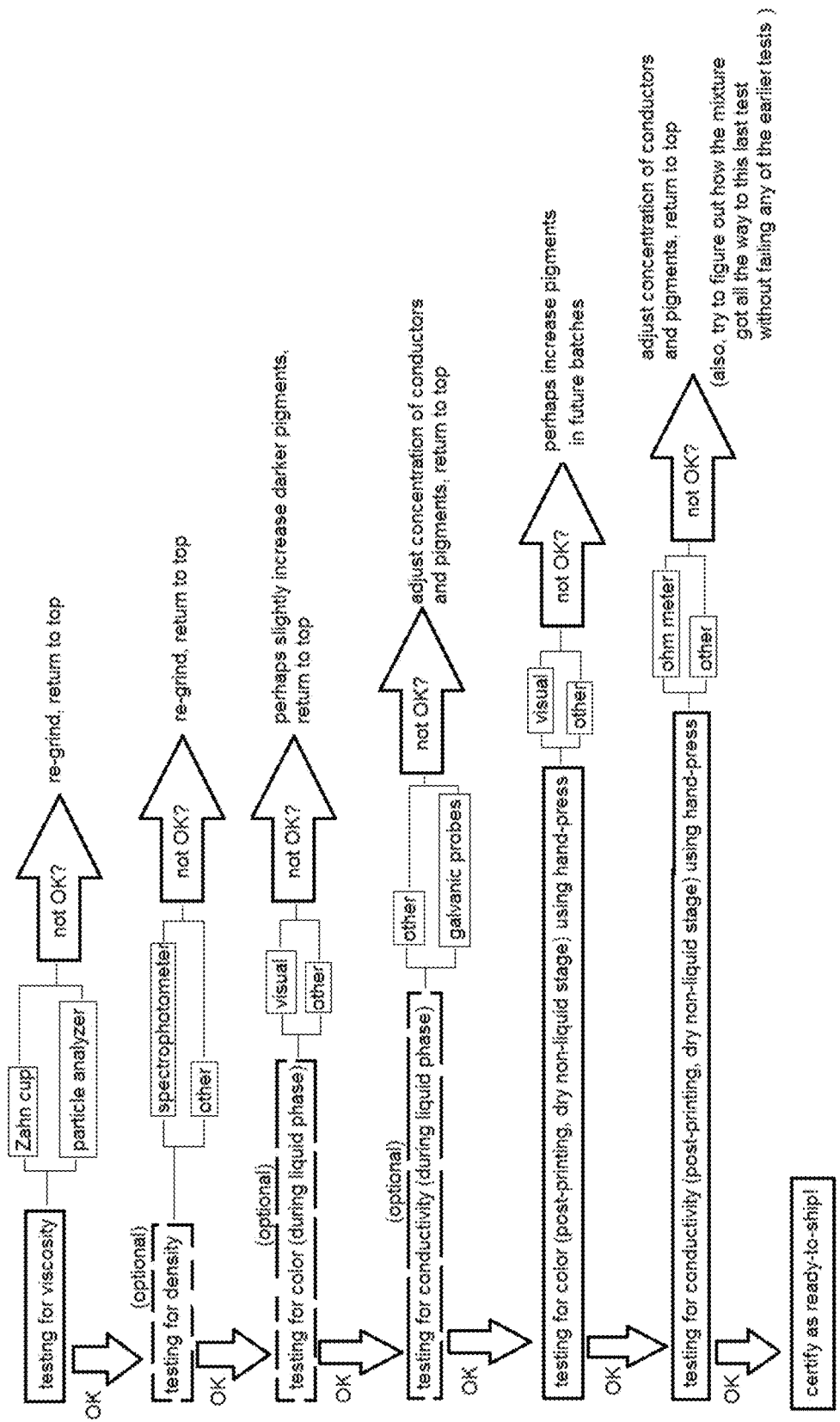

Another way to keep an eye on proper outcomes would be to do density testing using, for example, a spectrophotometer as shown in FIG. 6C. However, this can be expensive, and require a high level of skill. A Zahn cup test is easier to train people.

After passing through the Cowles disperser 504, or a disperser with a Cowles blade, a diaphragm pump can pump the material through the e.g. horizontal media mill 508. There are multiple ways to perform grinding, including actually pumping the liquid through the media mill 508 and then into another vessel. Further, that same mixture could then be pumped through the media mill 508 back into the original vessel 528, and so on and so on. In doing so, one can measure a grinding process by number of passes. That is, after the ink mixture 500 has made a pass through the media mill 508, then measure e.g. viscosity. After a second pass through the media mill 508, measure viscosity again.

It's also possible to put the mixture into a re-circulation path, i.e. actually only using one vessel 528 and circulating into the media mill 508 and then back into the vessel 528. Rather than iteratively measuring something, the recirculating can be done for a certain amount of time. Iterate through the media mill 508 until the micron sizes have been brought to acceptable levels.

Testing for proper micro-size can also be done with a particle size analyzer, but this is expensive and not conducive to low-cost setups.

If the ink mixture 500 is not sufficiently grinded, there is no reason to go onto other quality tests. Instead, more grind-time is needed. Keep doing the grinding, re-test, until the ink mixture 500 is below 6.5 µm.

Another way to assist in quality assurance and proper particle size can be filter-bags that are adjusted to a certain micron-size. Some build-up can occur on the edge of the vessel or bowl 528 of the Cowles disperser 504, so filter-bags can help remove this. This build-up is unlikely to be sufficiently grinded to be below 6.5 on the Hegman scale. Meanwhile, the filter-bags can be chosen and adjusted to a certain micron-size. Accordingly, such filter bags could act to keep the non-uniform build-up out of the main solution of the ink mixture 500.

Color Testing

Within the embodiments herein, any color-matching that occurs is mostly matching black. It's pretty easy to acclimate black to look like black, and not change or fade. Imagine a blue however, the ability to make the blue much lighter or much darker, or appear different, is more difficult. Fortunately, matching black with carbon is pretty easy with carbon being the main pigment. The color of graphite is kind of silvery and grayish, which does not create a conflict or color-clash with black.

With carbon involved, a black strip is created for the electrode 204. One can quickly see, just by eyeball, whether a uniformly black strip is achieved. One exception might be if the printer decided to add inordinate amounts of solvent. For some reason, printer personnel might drop the viscosity to 16 instead of running at 24-26, and add twice the amount of 80-20 that is typical. It's not clear why a printer would do this, but for example purposes let's assume this scenario happens. If so, that printer is technically diluting the product (bad). Such a short-cut could cause issues with the strength of coloration, to shift color. A black color might look more gray and less black. There is also a possibility if that printer were to do something like that, some of the conductivity might also be lost, because they would not be transferred as much solids (conductors) as what is typically printed at a higher viscosity. To address this, a printer could add pigment back to the ink mixture 500 and calibrate color by sight.

Working with the printers as service providers is an important consideration within the embodiments herein, and thus will be discussed in more detail at various places within this disclosure.

Hand Proofer Testing

Quality control checks on the end of formation of the ink mixture 500 is to ensure making of a consistent product every time, and that nothing is varying. One way to achieve this is to print with a hand-proofer which simulates a flexo-printer reaction without the expense of an actual flexo-printer on hand. A hand proofer of 165 lines, or 165 cells/inch, occupying e.g. 8.7 billion cubic microns in volume, would be suitable. One could pull a print twice to simulate\emulate the double pass (double bump) that is being done with the resulting garment 200 (as described elsewhere herein).

Then, it is possible to test with a regular conductivity meter, e.g. ohm-meter, to ensure one of numerous desired thresholds, e.g. 40 ohms. One could pick an abundant, low-cost, and known-consistent test-substrate easily available at the ink-creation lab. This way, the ink-developer (not the printer) can make the same style print with the same proofing device.

Now assume confirmation that the grind is satisfactory. Also assume the ink mixture 500 was "let down" (discharged from Cowles disperser mixer 504) so that the final flush has occurred, and thus the ink-mixture 500 is at the "let-down" phase 512 shown in FIG. 5A. However, also assume the ink mixture 500 is still in its liquid stage and hasn't been printed on anything yet.

As shown in FIGS. 6B and 6C, at this point, it might be suitable to do another check, e.g. color. As stated, with a black carbon and graphite combination, colors would be pretty easy to check. Unless some things drastically wrong like there's half the amount of components are supposed to be in there, such a problem is likely to have already been noted in earlier tests before getting to color-testing. So, for the embodiments herein, the color-testing will be easier, just check for sufficient blackness, the naked eye (e.g. "visual" check in FIG. 6C) would probably be sufficient. However, for more complex mixtures, a color-measurement device such as a spectrophotometer could be employed.

FIG. 6C is a more complex version of the testing structure shown in FIG. 6B. FIG. 6C shows alternatives ways of achieving each test. Including this all information within one Figure made that Figure difficult to grasp, so FIGS. 6B and 6C split out this testing information.

All this testing creates possibilities of inconsistent test results. To address this, sometimes move to different substrates to make the testing more consistent. From there, test for conductivity. The conductivity testing must occur where the carbons and graphites are first added. This way, errors can be detected early in the production process. Testing means that it's under 40 ohms. It is possible to test conductivity at the liquid phase, using for example galvanic probes (see FIG. 6C), thus heading off possible problems prior to the hand-press stage (FIGS. 6B and 6C) rather than after.

As stated, one precaution sometimes used is to have a "shipping viscosity" higher than an actual printing viscosity ("run" viscosity), because it's easier to dilute viscosity downwards than upwards. However, every once in a while, that causes problems because there's some printer vendors that don't understand that their the control over viscosity actually helps all parties immensely. Instead, these persons may want something where they merely open a bucket, and don't think, and put such a bucket on its printing press right away. This might be called a "press-ready bucket". What happens with the press ready bucket is "OK you want to press-ready, so we will ship out an ink-mixture 500 measuring between 24 and 26 on a 2-Zahn". Unfortunately, the workers clean the press up and when in washout phase, every hose on their press that has a dip therein holds an un-accounted ¼ Cup to ½ Cup of water. Accordingly, when they put the ink on, fire the press up, all that water comes out of the press and back into the ink, so their viscosity can go down to 20. And the printer-workers wonder why. Well, the reason why is that their working via a "press ready bucket" can be risky.

Now let's say a printer desired to do a production run at 24-26, but somehow the mixture got up to 30. It is possible to add a cup of 80-20 which all solvent-printers have, meaning 80% alcohol, 20% acetate blend, which would be an easy quick way to bring the ink mixture 500 from 30 back down to 24-26. Because acetate is very volatile, if it gets higher than 20 percent it will melt plates and swell rollers and components of the flexo press-machinery. It is desired to avoid this happening.

The embodiments herein strive to achieve effective levels of both coloration and conductivity. However, in the black-only embodiments, some flexibility in coloration exists.

Overgrinding

It is possible that someone may over grind so that is too far below 6.5 on the scale. This is possible but unlikely for a couple of reasons. Number one, grinding time is the biggest expense to the ink developer (as stated, different from the printer). So, most processes are always as tightly set up as possible to not be over grinding products. Whether that's based on the amount of passes or the amount of time, there is usually a mark in which checks are done very emphatically. An ink developer wants to get that back off their grinding machine as quickly as possible. Grinding a colored pigment grinding to a smaller than intended size could limit density of the ink mixture 500 and color strength, to some extent. Grinding consumes power, consumes labor, and other jobs may be waiting to use the grinding machinery.

Also, further grinding pigments to a smaller than intended amount would have very little to possibly no effect on conductivity of the resulting ink mixture 500. In the present embodiments of largely black colors, with the size of carbon and things being used in this, a detriment from over-grinding is unlikely.

Alcohol V. Water

Within the embodiments herein, water-based inks may also be suitable, but there are some differences in the printing process, because water doesn't dry nearly as fast as alcohol components. Alcohol-based inks dry fast, and for further efficiency, various of the embodiments herein take steps to push the drying speed to be even closer to the edge of the envelope.

Alcohol is considered a VOC. In an embodiment, an example formulation of the ink mixture 500 would have 33+/−3% solids, thus at a minimum 30% and maximum 36% solids. At that point, the remainder of the ink mixture 500 would be some type of VOC, a 60-66% VOC based solely in normal propyl alcohol, normal propyl acetate. The above aren't the worst VOCs that exist, but still, are VOCs. Drawbacks of VOCs will be discussed elsewhere.

Garment printing almost always is done with solvent-based inks, rather than water-based. Because of the thickness of the material and speeds they run at, and shouldn't be re-wet. These conditions are hard to achieve with water present. Meanwhile, alcohol and acetate are very water resistant.

In contrast, human urine has water content and thus might cause a water-based ink mixture to become liquid again and smear or tear down on the outside of a diaper or garment. Meanwhile, such a negative event occurring in a solvent system would be rare because it would take a specific type of alcohol to do so, and humans very seldom urinate this specific type of alcohol.

For determining whether an ink is water-based or solvent-based, there is one quick test. Take an unknown sample, not known whether water-based or solvent-based, and rub it with ammonia. If it comes off, its water-based. Next, rub the sample with alcohol. If it comes off, its solvent-based.

The flexographic printing process takes solid material which is generally through a range of 25-40%, and liquefies it. In the water-based world, it's all related to pH. Take alkali-soluble solids so that when reaching a pH range of 9.0-9.5, those solids want to liquefy.

Using an example of a water-based ink, assume an example of 30% solids which are liquified because the ink is alkali soluble and raised the pH level to 9.0-9.5. Then, upon printing, they put this thin layer down and through penetration in the substrate and evaporation of the amines, the pH level of the substance drops back down to a neutral 7.0 and all that remains are the solids (pigments).

Moving back to solvent-based printing, the resins and the pigments that are used are alcohol-soluble so that pH isn't involved anymore. Instead, the alcohol solubleizes (dissolves) the solids that are present. When printed, the alcohol and acetate, being VOCs, evaporate leaving only the resins and pigments (solids) behind.

With a flexo-printer, the facilities usually have a process center and mechanisms for handling solvent-based inks. For the ink maker (not the printer), solvent ink is a much bigger difficulty because it's harder to clean up. It's more volatile, more VOCs, there are air pollutants involved.

However, when solvent ink gets to the printer, solvent ink dries lighting fast, and viscosity can easily be adjusted, simply by adding to 80-20 blend to it. That is, if the ink-mixture gets too thick, just add some 80-20. Conversely, with water-based ink, one must keep pH just right, which is a lot more maintenance. With the solvent-based ink, all the effort is done in the creation of the ink, just keep the solvent-based ink at the proper viscosity.

At present, the solvent system being applied through a flexographic system is by far the most efficient way to produce the garments 200. This is for a variety of reasons. First, flexographic printing involves creating plates. Once the plates are created, the output of the resulting product becomes easier to manage. As such, solvent-based printing means less tendency for mistakes to be made and thus will be the most economical. There could be many ways, e.g. 3D printing, or do all kinds of stuff to make the conductive strips 204, but most would be less cost effective compared to flexographic printing. Also, flexographic production capacity is more prevalent, so a manufacturer can rent usage from a variety of vendors and service providers.

In general, diaper and garment products seldom want to use a water-based ink. Most facilities that are printing that type of work are set up to do solvent-based.

Solvent-based printing and preparation does have some inconveniences. The equipment has to be explosion proof, must have certain kind of containers according to a specific municipality, have a splitter, have to keep waste to some extent, and may have to recycle waste in some way. Further, venting has to be correct. So, there's more that goes into the regulations and set up of a solvent operation. But once set up, a flexographic system is probably the easiest to work with.

Moving back to the grinding of a solid material, it is often difficult to grind solid materials and particularly pigment into water because the surface tension of water is different than of solvents. In dropping solvent onto a piece of plastic it spreads out. But when dropping onto the same plastic water, the water beads up. The surface tension of water is not very conducive to making a pigment want to "wet out" (properly disperse). Consequently, using water-based inks requires an inordinate amount of dispersants, special things that have low molecular weights that will drop the surface tension of water and allow the pigment to "wet out". Still, there can be embodiments in which water-based inks are advantageous.

In contrast, alcohol and acetate are low surface tension solvents to begin with, so pigments like them are suitable when trying to get a blend of special agents such as the carbon and graphite combinations discussed herein. This is an advantage of using solvents that have a very low surface tension, and high wettability.

In the embodiments herein, the ink mixture 500 can probably be printed to a range from as thin as 20-22 seconds up to probably 35 seconds in a 2-Zahn. One would see relatively little difference in the products. The thicker product (higher number in the 2-Zahn) would probably make a slightly darker line, and may be ever so slightly more conductive.

At this point, all testing and quality control checks are completed. The ink mixture 500 product is deemed consistent and can be packaged and shipped.

Alternative Embodiments

The embodiments herein could have an alternative embodiment potentially focus on a water-based ink, not solvent-based. An embodiment that is not electrographic based, but some other printing arrangement also exists.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations, or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations, or equivalents. It is intended that the following claims define the scope of the invention and that methods and structures within the scope of these claims and their equivalents be covered thereby.

The invention claimed is:

1. A method of manufacturing conductive inks, comprising:
    combining a combination of carbon and graphite pigments, and solvent at a predetermined ratio;
    mixing the combination using a pre-mixer;
    monitoring the rate at which the pigments are combined with the solvent, to avoid overloading the pre-mixer;
    forcing the mixed combination through a media grinding mill;
    recirculating the mixed combination repeatedly through the media grinding mill and the pre-mixer; drying the mixed combination for one of a plurality of predetermined drying periods; and
    aggregating and packaging a completed mixture in a container suitable for shipping to a printer.

2. The method of claim 1, further comprising:
    performing the manufacturing steps at a first location, and performing one or more printing steps at a second location.

3. The method of claim 1, further comprising:
    the printer being flexographic.

4. The method of claim 3, further comprising:
    manufacturing the conductive inks to be alcohol-based.

5. The method of claim 4, further comprising:
    forming the solvent to be an alcohol-based solution.

6. The method of claim 1, further comprising:
    manufacturing the conductive inks to be water-based.

7. The method of claim 1, further comprising:
    selecting the carbon and graphite pigments for inclusion in the combination based on their conductivity;
    mixing the carbon pigments, graphite pigments, and the solvent in a mixing system using the pre-mixer; thereby dispersing the carbon and graphite pigments.

8. The method of claim 1, further comprising:
    grinding the carbon and graphite pigments to be below a predetermined size limit;
    measuring the size of the pigments;
    if the pigments are below a predetermined size limit, stopping the grinding; and
    if the pigments are not below the predetermined size limit, continuing the grinding.

9. The method of claim 8, further comprising:
    the predetermined size limit being 6.5 Microns or below.

10. The method of claim 8, further comprising:
    the pre-mixer containing a sawtooth blade.

11. The method of claim 1, further comprising:
the solvent comprising a combination of Normal propyl alcohol and Normal propyl acetate at an 80%-20% proportion.

12. The method of claim 8, further comprising:
configuring the pre-mixer to ensure a vortex occurs below the sawtooth blade.

13. The method of claim 8, further comprising:
loading the media grinding mill with grinding media of a predetermined shape, size, and consistency.

14. The method of claim 13, further comprising:
the grinding media comprising any one of steel beads, glass beads, synthetic bead, or a non-bead shape.

15. The method of claim 13, further comprising:
the predetermined grinding media size comprising approximately ten times the predetermined size limit of the pigments being grinded.

16. The method of claim 1, further comprising:
the media grinding mill being a horizontal media grinding mill.

* * * * *